(12) United States Patent
Iwasaki

(10) Patent No.: US 11,534,059 B2
(45) Date of Patent: Dec. 27, 2022

(54) ENDOSCOPE CONNECTION TUBE AND ENDOSCOPE REPROCESSOR

(71) Applicant: OLYMPUS CORPORATION, Tokyo (JP)

(72) Inventor: Tomokazu Iwasaki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 833 days.

(21) Appl. No.: 16/434,355

(22) Filed: Jun. 7, 2019

(65) Prior Publication Data

US 2019/0282079 A1 Sep. 19, 2019

Related U.S. Application Data

(63) Continuation of application No. PCT/JP2017/035872, filed on Oct. 2, 2017.

(30) Foreign Application Priority Data

Mar. 15, 2017 (JP) .............................. JP2017-050067

(51) Int. Cl.
 *A61B 1/12* (2006.01)
 *A61B 1/00* (2006.01)

(52) U.S. Cl.
 CPC .............. *A61B 1/125* (2013.01); *A61B 1/00* (2013.01); *A61B 1/12* (2013.01); *A61B 1/123* (2013.01)

(58) Field of Classification Search
 None
 See application file for complete search history.

(56) References Cited

U.S. PATENT DOCUMENTS

| 5,795,403 A | 8/1998 | Biermaier |
| 2007/0169799 A1* | 7/2007 | Noguchi ................. G01M 3/26 15/301 |
| 2012/0118338 A1 | 5/2012 | Nakanishi |

(Continued)

FOREIGN PATENT DOCUMENTS

| EP | 2481344 A1 | 8/2012 |
| EP | 3011893 A1 | 4/2016 |
| JP | 2004-135946 A | 5/2004 |

(Continued)

OTHER PUBLICATIONS

International Search Report dated Dec. 19, 2017 issued in PCT/JP2017/035872.

*Primary Examiner* — Cristi J Tate-Sims
(74) *Attorney, Agent, or Firm* — Scully, Scott, Murphy & Presser, P.C.

(57) ABSTRACT

An endoscope connection tube includes a fluid feeding pipeline that has a first end portion connected to a pipe sleeve of an endoscope, and a second end portion connected to a fluid supply source; a seal portion that is provided in the first end portion of the fluid feeding pipeline, includes a close contact surface configured to closely contact the pipe sleeve to surround an opening portion of the pipe sleeve, and is configured to connect an inside of the fluid feeding pipeline and an inside of the opening portion when the close contact surface closely contacts the pipe sleeve; and a detection pipeline that has a first end portion opened in the close contact surface, and is configured to be closed by the pipe sleeve when the close contact surface is in close contact with the pipe sleeve.

20 Claims, 17 Drawing Sheets

(56) References Cited

U.S. PATENT DOCUMENTS

2016/0135667 A1\* 5/2016 Takazawa .......... A61B 1/00128
134/166 C

FOREIGN PATENT DOCUMENTS

| JP | 2009-195400 A | 9/2009 |
| --- | --- | --- |
| WO | WO 2012/005089 A1 | 1/2012 |
| WO | WO 2015/174231 A1 | 11/2015 |

\* cited by examiner

ENDOSCOPE CONNECTION TUBE AND ENDOSCOPE REPROCESSOR

CROSS REFERENCE TO RELATED APPLICATION

This application is a continuation application of PCT/JP2017/035872 filed on Oct. 2, 2017 and claims benefit of Japanese Application No. 2017-050067 filed in Japan on Mar. 15, 2017, the entire contents of which are incorporated herein by this reference.

BACKGROUND OF INVENTION

1. Field of the Invention

The present invention relates to an endoscope connection tube for supplying a fluid into a pipeline included by an endoscope, and to an endoscope reprocessor.

2. Description of the Related Art

Endoscopes that are used in the medical field are subjected to reprocessing by using a medicinal solution such as an antiseptic solution after use. As disclosed in Japanese Patent Application Laid-Open Publication No. 2009-195400, for example, there is known an endoscope cleaning and disinfecting apparatus that automatically performs reprocessing to an endoscope. The endoscope cleaning and disinfecting apparatus disclosed in Japanese Patent Application Laid-Open Publication No. 2009-195400 includes a cleaning tube for supplying a fluid into a pipeline included by an endoscope. The cleaning tube connects a fluid supply portion that supplies a fluid and a pipe sleeve.

The cleaning tube disclosed in Japanese Patent Application Laid-Open Publication No. 2009-195400 has a seal member in a connection portion to the pipe sleeve of the pipeline of an endoscope, and is capable of switching a state where the seal member is in close contact with the pipe sleeve, and a state where the seal member is separated from the pipe sleeve. The cleaning tube disclosed in Japanese Patent Application Laid-Open Publication No. 2009-195400 having a configuration like this is capable of switching between a mode of feeding all of the fluid into the pipeline, and a mode of leaking a part of the fluid to the periphery of the pipe sleeve. The mode of feeding all of the fluid in the cleaning tube into the pipeline is selected when it is determined whether or not clogging occurs in the pipeline based on the measurement result of the flow rate of the fluid which is fed into the pipeline of the endoscope.

SUMMARY OF THE INVENTION

An endoscope connection tube according to one aspect of the present invention includes a fluid feeding pipeline that has a first end portion connected to a pipe sleeve of an endoscope, and a second end portion connected to a fluid supply source; a seal portion that is provided in the first end portion of the fluid feeding pipeline, includes a close contact surface configured to closely contact an outer surface of the endoscope to surround an opening portion of the pipe sleeve, and is configured to connect an inside of the fluid feeding pipeline and an inside of the opening portion when the close contact surface closely contacts the outer surface of the endoscope; and a detection pipeline that has a first end portion opened in the close contact surface, and is configured to be closed by the outer surface of the endoscope when the close contact surface is in close contact with the outer surface of the endoscope.

An endoscope reprocessor according to one aspect of the present invention includes the endoscope connection tube, a fluid supply source that is connected to the second end portion of the fluid feeding pipeline and a second end portion of the detection pipeline of the endoscope connection tube, and a first detection portion configured to detect a flow of a fluid in the detection pipeline, wherein the fluid supply source includes a fluid delivery pump, a delivery pipeline configured to connect the fluid delivery pump and the second end portion of the fluid feeding pipeline to each other, a detection fluid delivery pipeline configured to connect the delivery pipeline and the second end portion of the detection pipeline, and a three-way valve placed in a connection portion of the delivery pipeline and the detection fluid delivery pipeline, and the first detection portion is placed in a section between the fluid delivery pump and the three-way valve of the delivery pipeline.

DETAILED DESCRIPTION OF THE PREFERRED EMBODIMENT(S)

Figure 1:
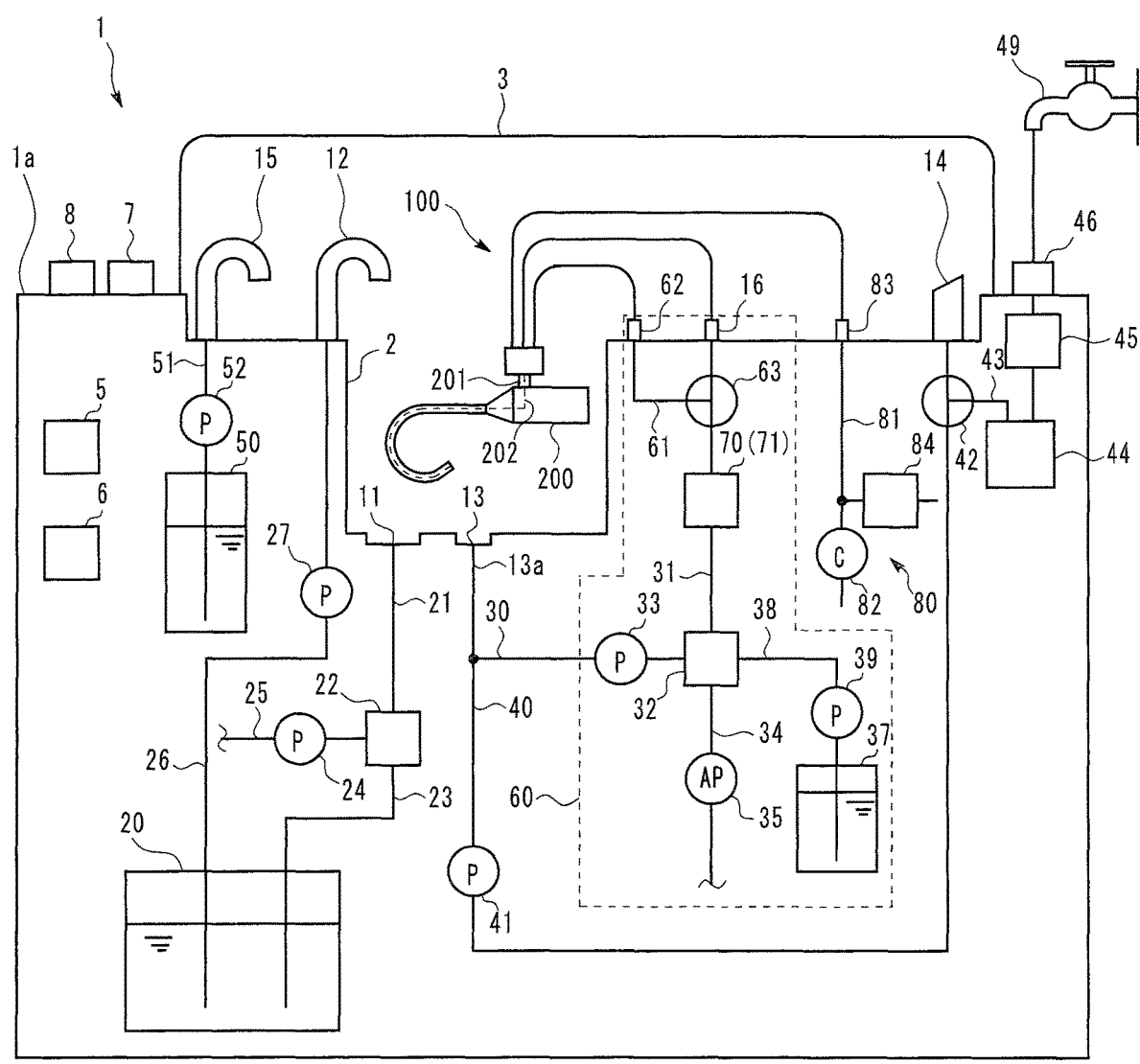
FIG. 1 is a diagram illustrating a configuration of an endoscope reprocessor of a first embodiment.

Hereinafter, a preferable mode of the present invention will be described with reference to the drawings. Note that in the respective drawings for use in the following explanation, in order to make respective components have such sizes as to be recognizable in the drawings, scales are made to be different for each of the components, and the present invention is not limited only to quantities of the components, shapes of the components, ratios of the sizes of the components, and relative positional relationships of the respective components that are illustrated in the drawings.

First Embodiment

Hereinafter, one example of an embodiment of the present invention will be described. An endoscope connection tube 100 is for connecting a fluid supply source 60 that feeds a fluid, and an inside of a pipeline 201 included by an endoscope 200. In a state where the fluid supply source 60 and the pipeline 201 are connected, the fluid which is fed from the fluid supply source 60 is fed into the pipeline 201 via the endoscope connection tube 100.

As illustrated in FIG. 1, in the present embodiment, as an example, the fluid supply source 60 is included in an endoscope reprocessor 1. The endoscope reprocessor 1 is an apparatus that applies reprocessing to the endoscope 200. The reprocessing mentioned here is not specially limited, but may be any one of rinse treatment with water, cleaning treatment to remove dirt such as organic matters, disinfection treatment to inactivate predetermined microorganisms, sterilization treatment to eliminate or kill all microorganisms, or combinations of the treatments.

Note that in the following explanation, an upper side refers to a position further away from the ground with respect to a comparison object, and a lower side refers to a position closer to the ground with respect to the comparison object. Further, high and low indicate a height relationship along gravity direction.

The endoscope reprocessor 1 includes a control unit 5, a power supply portion 6, a treatment basin 2, the fluid supply source 60 and a working fluid supply source 80.

The control unit 5 can be configured to include an arithmetic apparatus (CPU), a storage apparatus (RAM), an auxiliary storage apparatus, an input/output apparatus, a power control apparatus and the like, and has a configuration of executing a predetermined program in accordance with an instruction from a user, and controlling operations of respective parts configuring the endoscope reprocessor 1. Operations of the respective components included in the endoscope reprocessor 1 in the following explanation are controlled by the control unit 5 even when not specially stated.

An operation portion 7 and a display portion 8 configure a user interface that performs giving and receiving of information between the control unit 5 and the user. The operation portion 7 includes an operation member that receives an operation instruction from the user, such as a push switch and a touch sensor. The operation instruction from the user is converted into an electric signal by the operation portion 7, and is inputted to the control unit 5. The operation instruction from the user refers to a start instruction of reprocessing, for example. Note that the operation portion 7 may be in a form of being included by electronic equipment that performs wired communication or wireless communication with the control unit 5 and is separated from a main body portion 1a of the endoscope reprocessor 1.

The display portion 8 includes, for example, a display apparatus that displays images and letters, a light emitting apparatus that emits light, a speaker that generates sound, a vibrator that generates vibration, or a combination of these apparatuses. The display portion 8 outputs information to the user from the control unit 5. Note that the display portion 8 may be in a mode of being included by electronic equipment that performs wired communication or wireless communication with the control unit 5 and is separated from the main body portion 1a of the endoscope reprocessor 1.

The power supply portion 6 supplies power to the respective parts of the endoscope reprocessor 1. The power supply portion 6 distributes power obtained from an outside such as a commercial power supply to the respective parts. Note that the power supply portion 6 may include a power generation apparatus and a battery.

The treatment basin 2 is in a recessed shape having an opening portion, and is capable of storing a liquid inside. In the treatment basin 2, the endoscope 200 can be disposed. In the treatment basin 2, a plurality of endoscopes 200 may be able to be disposed.

At an upper part of the treatment basin 2, a lid 3 configured to open and close the opening portion of the treatment basin 2 is provided. When reprocessing is applied to the endoscope in the treatment basin 2, the opening portion of the treatment basin 2 is closed by the lid 3.

In the treatment basin 2, a cleaning solution nozzle 15, a medicinal solution nozzle 12, a drain port 11, a circulation port 13, a circulation nozzle 14, an endoscope pipeline connection portion 16, a detection pipeline connection portion 62, and a working fluid pipeline connection portion 83 are provided.

The cleaning solution nozzle 15 is an opening portion that communicates with the cleaning solution tank 50 that stores a cleaning solution, via a cleaning solution pipeline 51. The cleaning solution is used in cleaning treatment. In the cleaning solution pipeline 51, a cleaning solution pump 52 is provided. The cleaning solution pump 52 is connected to the control unit 5, and an operation of the cleaning solution pump 52 is controlled by the control unit 5. By operating the cleaning solution pump 52, the cleaning solution in the cleaning solution tank 50 is transferred into the treatment basin 2.

The medicinal solution nozzle 12 is an opening portion that communicates with a medicinal solution tank 20 via a medicinal solution pipeline 26. The medicinal solution tank 20 stores a medicinal solution. A kind of the medicinal solution stored by the medicinal solution tank 20 is not specially limited, but in the present embodiment, as an example, an antiseptic solution for use in disinfection treatment, or a sterilization solution for use in sterilizing treatment. As the antiseptic solution or the sterilization solution, a peracetic acid aqueous solution is cited.

A medicinal solution pump 27 is provided in the medicinal solution pipeline 26. By operating the medicinal solution pump 27, a medicinal solution in the medicinal solution tank 20 is transferred into the treatment basin 2 via the medicinal solution pipeline 26 and the medicinal solution nozzle 12.

In the present embodiment, as an example, the medicinal solution is reusable when the medicinal solution has an effect of medicine even after the medicinal solution is used in reprocessing. Accordingly, the endoscope reprocessor 1 includes a configuration of recovering the medicinal solution in the treatment basin 2 and returning the medicinal solution into the medicinal solution tank 20. The configuration of recovering the medicinal solution in the treatment basin 2 and returning the medicinal solution into the medicinal solution tank 20 will be described later.

The drain port 11 is an opening portion provided in a lowest spot in the treatment basin 2. The drain port 11 is connected to a discharge pipeline 21. The discharge pipeline 21 causes the drain port 11 and a switch valve 22 to communicate with each other. A recovery pipeline 23 and a disposal pipeline 25 are connected to the switch valve 22. The switch valve 22 is switchable to a state of closing the discharge pipeline 21, a state of causing the discharge pipeline 21 and the recovery pipeline 23 to communicate with each other, or a state of causing the discharge pipeline 21 and the disposal pipeline 25 to communicate with each other. The switch valve 22 is connected to the control unit 5, and an operation of the switch valve 22 is controlled by the control unit 5.

The recovery pipeline 23 causes the medicinal solution tank 20 and the switch valve 22 to communicate with each other. The disposal pipeline 25 causes a drain facility for receiving a liquid discharged from the endoscope reprocessor 1 and the switch valve 22 to communicate with each other.

When the switch valve 22 is brought into a closed state, the liquid can be stored in the treatment basin 2. When the switch valve 22 is brought into a state where the discharge pipeline 21 and the recovery pipeline 23 communicate with each other when the medicinal solution is stored in the treatment basin 2, the medicinal solution is transferred to the medicinal solution tank 20 from the treatment basin 2. When the switch valve 22 is brought into the state where the discharge pipeline 21 and the disposal pipeline 25 communicate with each other, the liquid in the treatment basin 2 is fed to the drain facility via the disposal pipeline 25. Note that in the present embodiment, as an example, the disposal pipeline 25 is provided with the drain pump 24 for promoting drain of the liquid from the treatment basin.

The circulation port 13 is an opening portion provided in a vicinity of a bottom surface of the treatment basin 2. The circulation port 13 communicates with a circulation pipeline 13a. The circulation pipeline 13a branches into two pipelines that are an endoscope circulation pipeline 30 and a treatment basin circulation pipeline 40.

The endoscope circulation pipeline 30 causes the circulation pipeline 13a and a channel block 32 that will be described later to communicate with each other. The endoscope circulation pipeline 30 is provided with a fluid delivery pump 33. The fluid delivery pump 33 transfers a fluid in the endoscope circulation pipeline 30 toward the channel block 32 by being operated.

To the channel block 32, an intake pipeline 34, an alcohol pipeline 38 and a delivery pipeline 31 are connected, in addition to the aforementioned endoscope circulation pipeline 30. The channel block 32 connects the delivery pipeline 31, the endoscope circulation pipeline 30, the intake pipeline 34 and the alcohol pipeline 38. The channel block 32 is provided with a check valve configured to allow a flow of the fluid in only a direction toward the channel block 32 from each of the endoscope circulation pipeline 30, the intake pipeline 34 and the alcohol pipeline 38. In other words, the fluid is prevented from flowing to the endoscope circulation pipeline 30, the intake pipeline 34 and the alcohol pipeline 38 from an inside of the channel block 32.

The intake pipeline 34 has one end portion opened to the atmosphere and the other end portion connected to the channel block 32. Note that a filter configured to filter gas that passes is provided at the one end portion of the intake pipeline 34 though not illustrated. An air pump 35 is provided in the intake pipeline 34 and transfers gas in the intake pipeline 34 to the channel block 32 by being operated.

The alcohol pipeline 38 causes an alcohol tank 37 configured to store alcohol and the channel block 32 to communicate with each other. As the alcohol stored in the alcohol tank 37, for example, ethanol is cited. An alcohol concentration can be arbitrarily selected. An alcohol pump 39 is provided in the alcohol pipeline 38, and transfers the alcohol in the alcohol tank 37 to the channel block 32 by being operated.

The fluid delivery pump 33, the air pump 35 and the alcohol pump 39 are connected to the control unit 5, and operations of the pumps are controlled by the control unit 5. When an operation of the fluid delivery pump 33 is started when the liquid is stored in the treatment basin 2, the liquid in the treatment basin 2 is pumped into the delivery pipeline 31 via the circulation port 13, the circulation pipeline 13a and the endoscope circulation pipeline 30. When an operation of the air pump 35 is started, air is pumped into the delivery pipeline 31. When an operation of the alcohol pump 39 is started, the alcohol in the alcohol tank 37 is pumped into the delivery pipeline 31.

The delivery pipeline 31 is connected to the endoscope pipeline connection portion 16. The endoscope pipeline connection portion 16 is connected to a pipe sleeve 202 provided in the endoscope 200 via the endoscope connection tube 100 that will be described later. The fluid that is fed to the delivery pipeline 31 from the channel block 32 is introduced into the pipeline 201 that communicates with the pipe sleeve 202 of the endoscope 200 via the endoscope pipeline connection portion 16.

The detection pipeline connection portion 62 and the working fluid pipeline connection portion 83 are parts to which the endoscope connection tube 100 that will be described later is connected.

The delivery pipeline 31, the fluid delivery pump 33, the endoscope pipeline connection portion 16 and the detection pipeline connection portion 62 configure the fluid supply source 60 that delivers the fluid and will be described later. The working fluid pipeline connection portion 83 configures the working fluid supply source 80 that delivers the working fluid and will be described later.

The treatment basin circulation pipeline 40 causes the circulation pipeline 13a and the circulation nozzle 14 to communicate with each other. The circulation nozzle 14 is an opening portion provided in the treatment basin 2. The treatment basin circulation pipeline 40 is provided with a liquid flowing pump 41. The liquid flowing pump 41 is connected to the control unit 5 and an operation of the liquid flowing pump 41 is controlled by the control unit 5.

A three-way valve 42 is provided between the liquid flowing pump 41 of the treatment basin circulation pipeline 40 and the circulation nozzle 14. A water supply pipeline 43 is connected to the three-way valve 42. The three-way valve 42 is capable of switching to a state of causing the circulation nozzle 14 and the treatment basin circulation pipeline 40 to communicate with each other, or a state of causing the circulation nozzle 14 and the water supply pipeline 43 to communicate with each other.

The water supply pipeline 43 causes the three-way valve 42 and a water supply source connection portion 46 to communicate with each other. The water supply pipeline 43 is provided with a water introduction valve 45 configured to open and close the water supply pipeline 43 and a water filter 44 configured to filter water. The water supply source connection portion 46 is connected to a water supply source 49 such as a water supply facility that delivers water, via a hose or the like.

The three-way valve 42 and the water introduction valve 45 are connected to the control unit 5, and operations of the valves are controlled by the control unit 5.

When the three-way valve 42 is brought into a state of causing the circulation nozzle 14 and the treatment basin circulation pipeline 40 to communicate with each other, and an operation of the liquid flowing pump 41 is started, in a case where the liquid is stored in the treatment basin 2, the liquid in the treatment basin 2 is ejected from the circulation nozzle 14 via the circulation port 13, the circulation pipeline 13a and the treatment basin circulation pipeline 40.

When the three-way valve 42 is brought into the state of causing the circulation nozzle 14 and the water supply pipeline 43 to communicate with each other, and the water introduction valve 45 is brought into an open state, water supplied from the water supply source 49 is ejected from the circulation nozzle 14. The water ejected from the circulation nozzle 14 is introduced into the treatment basin 2, and is used as rinse water or the like for rinsing the endoscope and the like disposed in the treatment basin 2.

Figure 2:
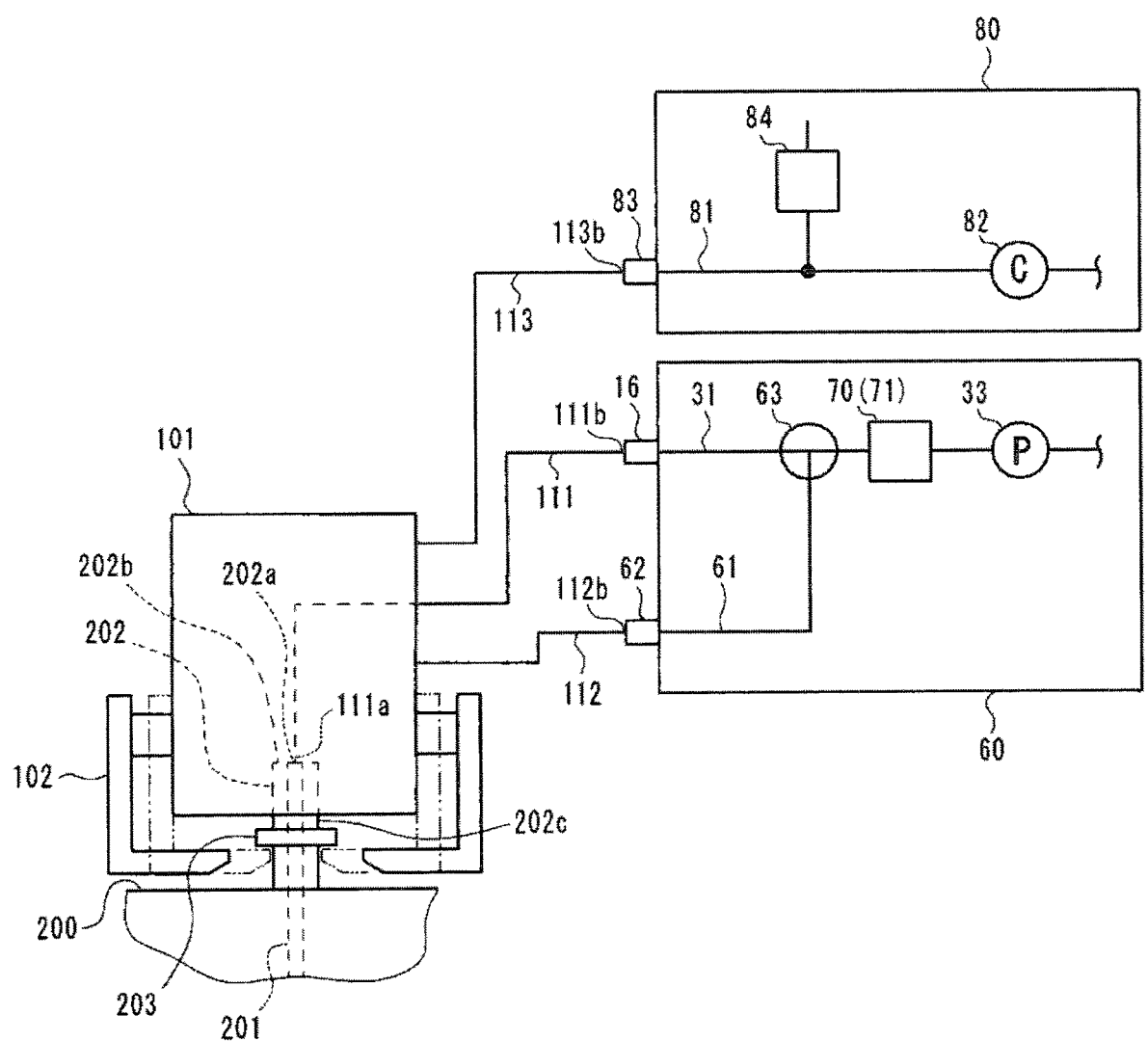
FIG. 2 is a diagram illustrating configurations of an endoscope connection tube, a fluid supply portion and a working fluid supply portion of the first embodiment.
Figure 3:
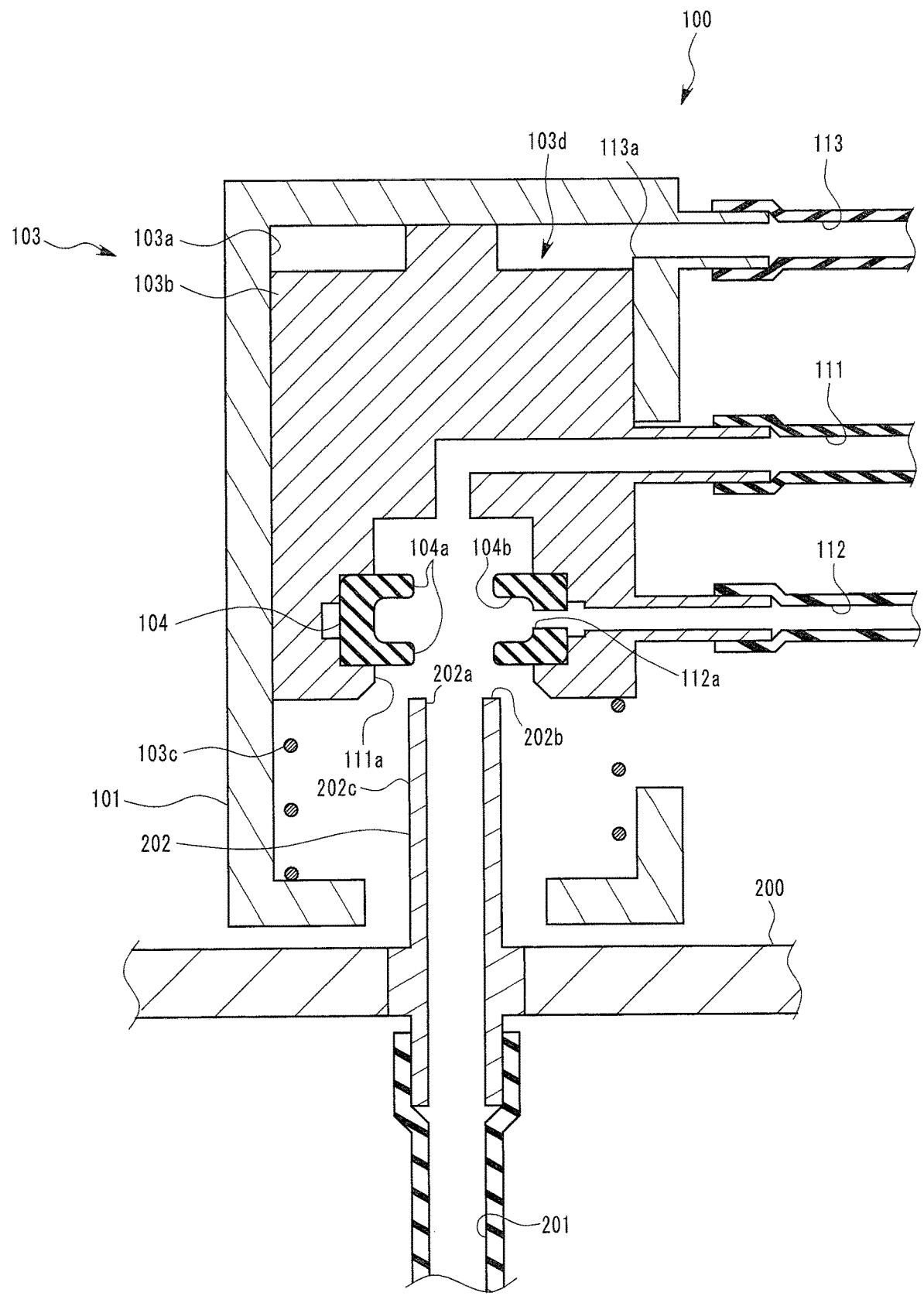
FIG. 3 is a sectional view illustrating a configuration of the endoscope connection tube of the first embodiment.
Figure 4:
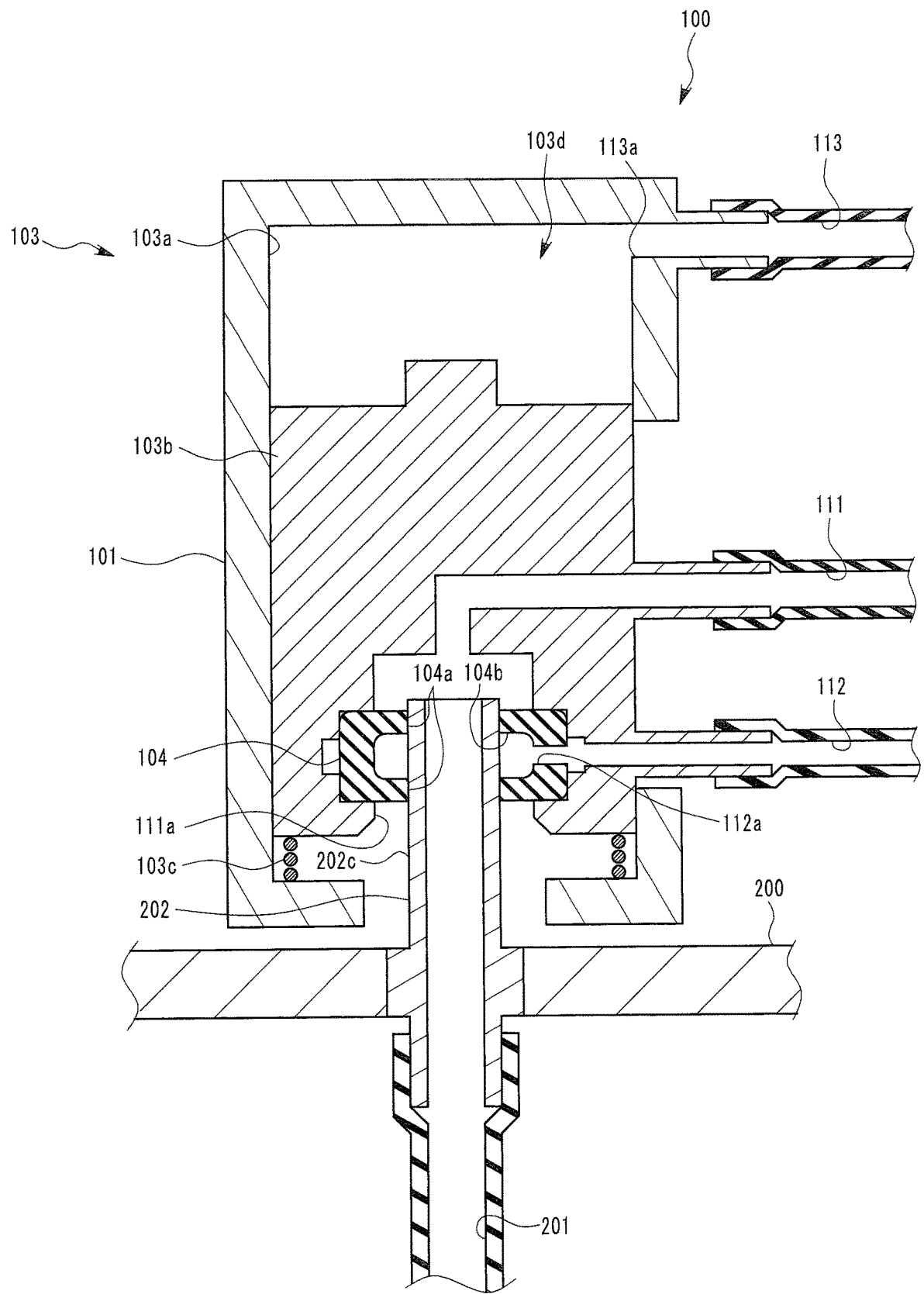
FIG. 4 is a sectional view illustrating the configuration of the endoscope connection tube of the first embodiment.

FIG. 2 is a diagram illustrating configurations of the fluid supply source 60, the working fluid supply source 80 and the endoscope connection tube 100. FIG. 3 and FIG. 4 are sectional views each illustrating a configuration of a connector portion 101 of the endoscope connection tube 100.

The fluid supply source 60 includes the endoscope pipeline connection portion 16 to which a fluid feeding pipeline 111 included by the endoscope connection tube 100 is connected, and the detection pipeline connection portion 62 to which a detection pipeline 112 included by the endoscope connection tube 100 is connected.

The fluid supply source 60 includes a configuration of delivering the fluid from the endoscope pipeline connection portion 16 and the detection pipeline connection portion 62. The configuration is not specially limited, but in the present embodiment, as an example, the fluid supply source 60 includes the three-way valve 63 that switches and guides the fluid delivered from the fluid delivery pump 33 that is a single pump to the endoscope pipeline connection portion 16 or the detection pipeline connection portion 62.

More specifically, the fluid supply source 60 includes the delivery pipeline 31 that connects the fluid delivery pump 33 and the endoscope pipeline connection portion 16, the detection fluid feed pipeline 61 that connects a section from the fluid delivery pump 33 to the endoscope pipeline connection portion 16 in the delivery pipeline 31 and the detection pipeline connection portion 62, and the three-way valve 63 provided in a connection portion of the delivery pipeline 31 and the detection fluid feed pipeline 61.

The three-way valve 63 is connected to the control unit 5, and an operation of the three-way valve 63 is controlled by the control unit 5. The three-way valve 63 can be switched to a state of guiding the fluid which is delivered from the fluid delivery pump 33 to the endoscope pipeline connection portion 16, and a state of guiding the fluid to the detection pipeline connection portion 62.

The fluid supply source 60 includes a flow rate measurement portion 71 configured to detect a flow rate of the fluid delivered from the endoscope pipeline connection portion 16, and a detection portion 70 configured to detect presence or absence of a flow of the fluid delivered from the detection pipeline connection portion 62. Configurations of the portions are not specially limited, but in the present embodiment, as an example, the flow rate measurement portion 71 configured to detect the flow rate of the fluid delivered from the fluid delivery pump 33 also serves as the detection portion 70. In other words, in the present embodiment, the flow rate measurement portion 71 and the detection portion 70 are integrated with each other. As the flow rate measurement portion 71 and the detection portion 70, for example, a flow rate sensor and/or a pressure sensor are used.

More specifically, the flow rate measurement portion 71 is disposed in a section from the fluid delivery pump 33 of the delivery pipeline 31 to the three-way valve 63, and measures a flow rate of a fluid flowing in the section. Accordingly, when the three-way valve 63 is in the state of causing the fluid delivery pump 33 and the endoscope pipeline connection portion 16 to communicate with each other, the flow rate measurement portion 71 can detect the flow rate of the fluid which is delivered from the endoscope pipeline connection portion 16. When the three-way valve 63 is in the state of causing the fluid delivery pump 33 and the detection pipeline connection portion 62 to communicate with each other, the flow rate measurement portion 71 can detect presence or absence of a flow of a fluid that is delivered from the detection pipeline connection portion 62. In this way, in the present embodiment, the flow rate measurement portion 71 also serves as the detection portion 70.

The working fluid supply source 80 includes a working fluid pipeline connection portion 83 to which a working fluid pipeline 113 included by the endoscope connection tube 100 is connected, and delivers a working fluid from the working fluid pipeline connection portion 83.

A form of the working fluid is not specially limited, but in the present embodiment, as an example, the working fluid is air. Accordingly, the working fluid supply source 80 includes an air compressor 82 configured to deliver air which is the working fluid with a predetermined pressure, and an air delivery pipeline 81 configured to connect the air compressor 82 and the working fluid pipeline connection portion 83. The air delivery pipeline 81 is provided with an exhaust valve 84 for exhausting internal air to an outside. The air compressor 82 and the exhaust valve 84 are connected to the control unit 5, and operations of the air compressor 82 and the exhaust valve 84 are controlled by the control unit 5. The air delivery pipeline 81 may be provided with a pressure regulator that adjusts pressure of the air that is delivered from the air compressor 82.

Note that the air compressor 82 may also serve as the air pump 35 included by the endoscope reprocessor 1. In this case, the endoscope reprocessor 1 includes a switch valve that switches the air delivered from the air compressor 82 to a state of being guided to the working fluid pipeline connection portion 83, and a state of being guided to the channel block 32.

Next, a configuration of the endoscope connection tube 100 will be described.

The endoscope connection tube 100 includes the connector portion 101, the fluid feeding pipeline 111, the detection pipeline 112 and the working fluid pipeline 113.

The endoscope connection tube 100 is an apparatus configured to guide a part or all of the fluid that is delivered from the endoscope pipeline connection portion 16 of the fluid supply source 60 into an opening portion 202a that is provided in the pipe sleeve 202 of the endoscope 200. The opening portion 202a of the pipe sleeve 202 communicates with the pipeline 201 included by the endoscope 200.

A shape of the pipe sleeve 202 is not specially limited, but in the present embodiment, as an example, the pipe sleeve 202 is in a cylindrical shape that protrudes from an outer surface of the endoscope 200, and the opening portion 202a is formed in an end surface 202b.

The connector portion 101 includes a holding portion 102 configured to hold the connector portion 101 so that the connector portion 101 faces the pipe sleeve 202 of the endoscope 200. In the present embodiment, as an example, the holding portion 102 engages with a locking portion 203 that is a protruded portion provided on a side surface 202c of the pipe sleeve 202 that is in a cylindrical shape, and holds the connector portion 101 in a predetermined position with respect to the pipe sleeve 202. Note that the holding portion 102 may have a configuration of engaging with a locking portion that is provided in a different position from the pipe sleeve 202 in the outer surface of the endoscope 200. Note that the smaller an area where the holding portion 102 and the locking portion 203 contact each other, the better.

FIG. 3 and FIG. 4 each illustrate a state where the holding portion 102 engages with the endoscope 200, and the connector portion 101 is held in a vicinity of the pipe sleeve 202. In FIG. 3 and FIG. 4, the holding portion 102 and the locking portion 203 are omitted and not illustrated.

A first end portion 111a of the fluid feeding pipeline 111 is opened in the connector portion 101. A second end portion 111b of the fluid feeding pipeline 111 is connectable to the endoscope pipeline connection portion 16 of the fluid supply source 60.

The first end portion 111a of the fluid feeding pipeline 111 is disposed in a position where the first end portion 111a faces the opening portion 202a of the pipe sleeve 202 and opens, in a state where the connector portion 101 is held in a vicinity of the pipe sleeve 202 by the holding portion 102.

A seal portion 104 is placed at the first end portion 111a of the fluid feeding pipeline 111. The seal portion 104 includes close contact surfaces 104a that closely contact the pipe sleeve 202 to surround the opening portion 202a of the pipe sleeve 202. The close contact surface 104a is in an annular shape, for example. FIG. 4 illustrates a state where the close contact surfaces 104a of the seal portion 104 is in close contact with the pipe sleeve 202. In the state where the close contact surface 104a is in close contact with the pipe sleeve 202, an inside of the fluid feeding pipeline 111 and an inside of the opening portion 202a of the pipe sleeve 202 are connected airtightly. In other words, in the state where the close contact surfaces 104a are in close contact with the pipe sleeve 202 as illustrated in FIG. 4, all the fluid that is delivered into the fluid feeding pipeline 111 from the fluid supply source 60 is introduced into the opening portion 202a of the pipe sleeve 202 without leaking to outside.

In the present embodiment, the seal portion 104 is an annular rubber member provided along an inner circumferential surface of the first end portion 111a of the fluid feeding pipeline 111, and the pipe sleeve 202 is fitted inside of the seal portion 104. The close contact surfaces 104a of the seal portion 104 closely contact the side surface 202c of the pipe sleeve 202 which is fitted in the seal portion 104 entirely in a circumferential direction.

A first end portion 112a of the detection pipeline 112 opens in the close contact surface 104a of the seal portion 104. In other words, a periphery of an opening of the first end portion 112a of the detection pipeline 112 is surrounded by the close contact surfaces 104a. Accordingly, in the state where the close contact surface 104a is in close contact with the pipe sleeve 202, the first end portion 112a of the detection pipeline 112 is closed.

A second end portion 112b of the detection pipeline 112 is connectable to the detection pipeline connection portion 62 of the fluid supply source 60. In the state where the close contact surface 104a is in close contact with the pipe sleeve 202 as illustrated in FIG. 4, the fluid in the detection pipeline 112 does not flow even when the fluid is delivered into the detection pipeline 112 from the fluid supply source 60.

Figure 5:
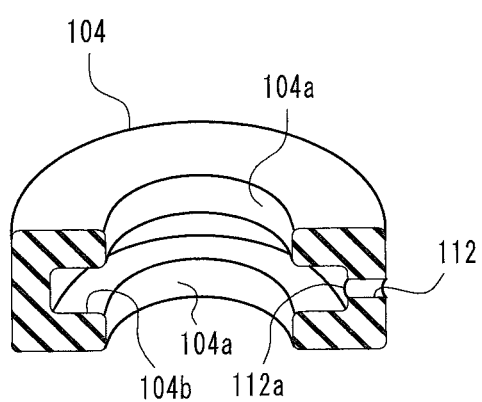
FIG. 5 is a sectional perspective view illustrating a shape of a seal portion of the first embodiment.

FIG. 5 is a sectional view illustrating shapes of the close contact surface 104a of the seal portion 104 and the first end portion 112a of the detection pipeline 112. As described above, the close contact surface 104a is in an annular shape which closely contacts the side surface 202c of the pipe sleeve 202 entirely in the circumferential direction. The seal portion 104 has an annular groove 104b that is provided along the close contact surface 104a in an extending direction in the close contact surface 104a which is in an annular shape. The first end portion 112a of the detection pipeline 112 opens into the groove 104b.

Accordingly, in the present embodiment, the detection pipeline 112 is closed by the side surface 202c only when the close contact surfaces 104a of the seal portion 104 are in close contact with the side surface 202c of the pipe sleeve 202 entirely in the circumferential direction. In other words, when a part of the close contact surfaces 104a is separated from the pipe sleeve 202, the detection pipeline 112 is not closed.

For example, when the first end portion 112a of the detection pipeline 112 opens in only one portion in the circumferential direction of the close contact surface 104a unlike the present embodiment, the detection pipeline 112 is closed when only the corresponding portion of the close contact surfaces 104a is in close contact with the opening. In this case, even when the close contact surface is separated from the pipe sleeve 202 in a spot except for the corresponding portion of the close contact surfaces 104a, the detection pipeline 112 is closed.

In the present embodiment, in a case where a defect such as a break occurs to a part of the seal portion 104, and the close contact surface 104a is separated partially from the pipe sleeve 202, the detection pipeline 112 can be reliably prevented from being closed. In other words, in the present embodiment, in a case where the close contact surfaces 104a are partially separated from the pipe sleeve 202, the fluid in the detection pipeline 112 flows when the fluid is delivered into the detection pipeline 112 from the fluid supply source 60.

The endoscope connection tube 100 of the present embodiment includes a switch portion 103 that causes the seal portion 104 to move between a first position where the close contact surfaces 104a are in close contact with the pipe sleeve 202, and a second position where the close contact surface 104a is separated from the pipe sleeve 202, in a state where the first end portion 111a of the fluid feeding pipeline 111 is held to face the pipe sleeve 202 by the holding portion 102. FIG. 3 illustrates a state where the seal portion 104 is located in the second position, and FIG. 4 illustrates a state where the seal portion 104 is located in the first position.

Movement of the seal portion 104 by the switch portion 103 may be in a mode of being performed by a force applied by a finger of a user of the endoscope reprocessor 1, for example, or may be in a mode of being performed by a force generated by a mechanism included by the endoscope reprocessor 1 or the endoscope connection tube 100, for example.

In the present embodiment, as an example, the switch portion 103 has a configuration of causing the seal portion 104 to move between the first position and the second position in response to pressure of the fluid supplied from the working fluid supply source 80.

More specifically, the switch portion 103 has a mode of a so-called pneumatic cylinder that includes a cylinder portion 103a that is a cylindrical space formed in the connector portion 101, and a piston-shaped moving portion 103b that moves to advance and retreat in the cylinder portion 103a. In the state where the first end portion 111a of the fluid feeding pipeline 111 is held to face the pipe sleeve 202 by the holding portion 102, the moving portion 103b approaches the pipe sleeve 202 when the moving portion 103b moves to one side in moving directions, and the moving portion 103b moves away from the pipe sleeve 202 when the moving portion 103b moves to one side in the moving directions.

In a surface facing one side in the moving direction of the moving portion 103b, the first end portion 111a of the fluid feeding pipeline 111 opens. In a space 103d which is defined by a surface facing the other side in the moving directions of the moving portion 103b and an inner wall of the cylinder portion 103a, a first end portion 113a of the working fluid pipeline 113 opens. A second end portion 113b of the working fluid pipeline 113 is connectable to the working fluid pipeline connection portion 83 of the working fluid supply source 80. The switch portion 103 includes an urging member 103c that urges the moving portion 103b to the other side in the moving directions of the moving portion 103b. The first end portion 111a of the fluid feeding pipeline 111 opens to the one side in the moving directions of the moving portion 103b.

In the switch portion 103 of the present embodiment configured as above, in a case where air at a predetermined pressure is supplied into the space 103d of the cylinder portion 103a from the working fluid supply source 80, the moving portion 103b moves in the direction to approach the pipe sleeve 202, and the close contact surface 104a of the seal portion 104 closely contacts the pipe sleeve 202, as illustrated in FIG. 4. Note that in order to enhance air tightness in the space 103d, a seal member such as an O-shaped ring may be provided between the cylinder portion 103a and the moving portion 103b.

When supply of the air from the working fluid supply source 80 is not performed, the moving portion 103b moves in a direction to be away from the pipe sleeve 202 by the urging force of the urging member 103c, and the close contact surface 104a of the seal portion 104 separates from the pipe sleeve 202, as illustrated in FIG. 3. Note that in the present embodiment, air is used as the working fluid, but the working fluid is not limited to air, but may be other gases or liquids.

As described above, in the endoscope connection tube 100 of the present embodiment, when the seal portion 104 is located in the first position where the seal portion 104 closely contacts the pipe sleeve 202, a total amount of the fluid that is delivered from the first end portion 111a of the fluid feeding pipeline 111 is fed into the pipeline 201. When the seal portion 104 is located in the second position where the seal portion 104 is separated from the pipe sleeve 202, in the endoscope connection tube 100 of the present embodiment, a part of the fluid that is delivered from the first end portion 111a of the fluid feeding pipeline 111 leaks to the periphery of the pipe sleeve 202, and remaining fluid is fed into the pipeline 201.

Figure 6:
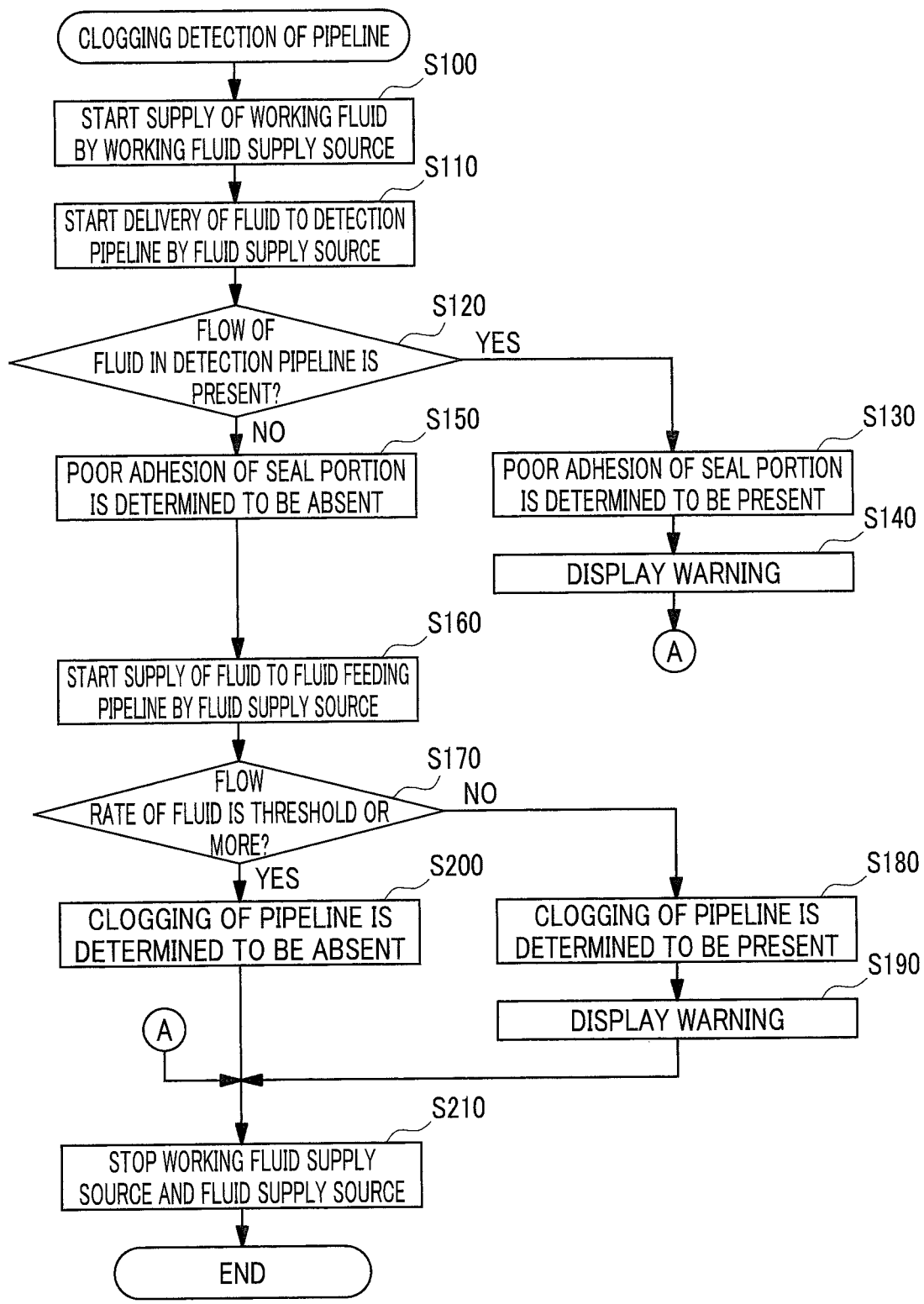
FIG. 6 is a flowchart illustrating a clogging detection operation of the first embodiment.
Figure 7:
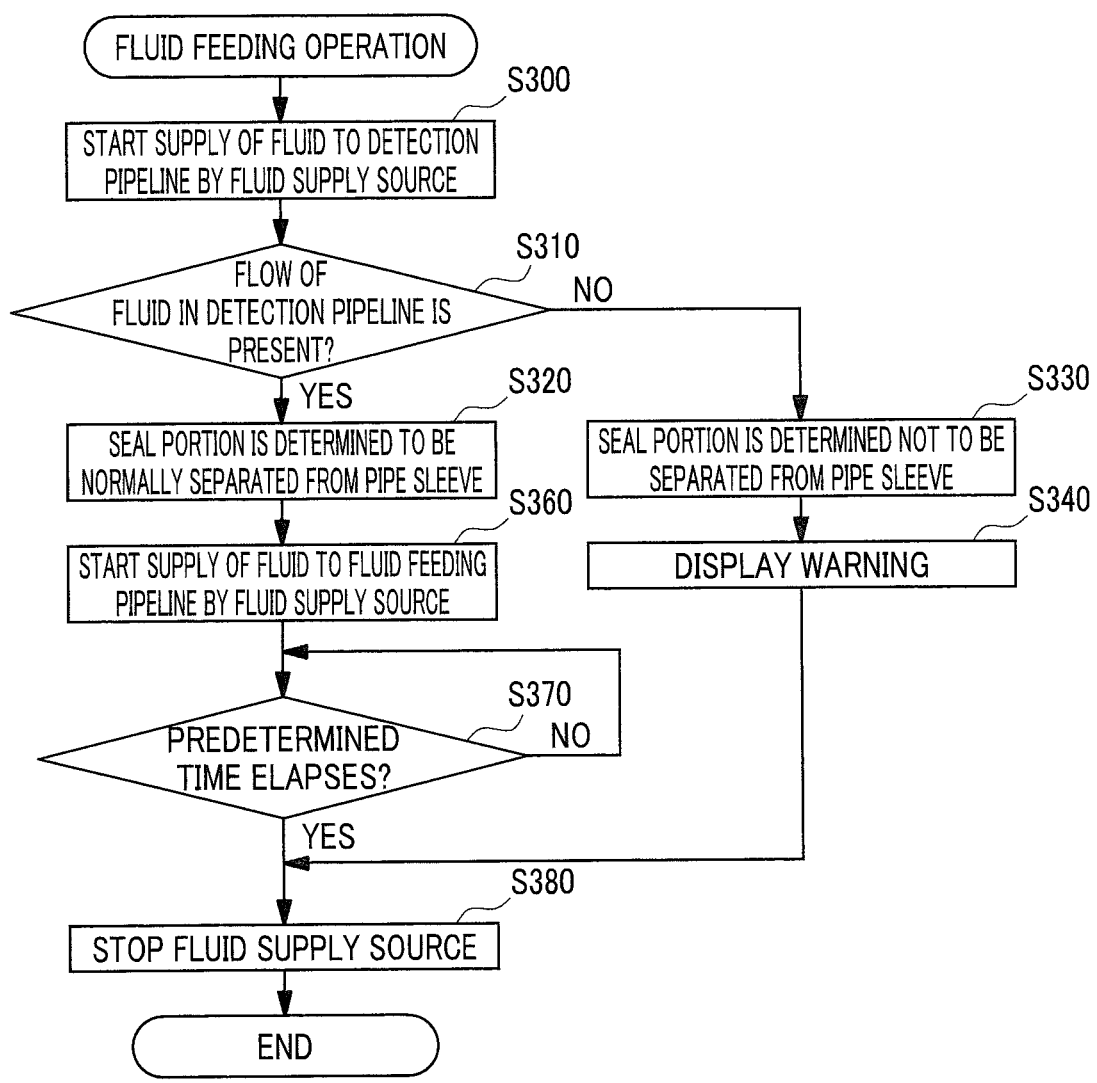
FIG. 7 is a flowchart illustrating a fluid feeding operation of the first embodiment.

Next, an operation of the endoscope reprocessor 1 including the endoscope connection tube 100 having the configuration described above will be described. FIG. 6 is a flowchart of control by the control unit 5 at a time of executing a clogging detection operation of detecting presence or absence of clogging such as blockage and constriction of the pipeline 201 included by the endoscope 200. FIG. 7 is a flowchart of control by the control unit 5 at a time of executing a fluid feeding operation of feeding the fluid into the pipeline 201 included by the endoscope 200.

The clogging detection operation illustrated in FIG. 6 is executed in an arbitrary step during reprocessing to the endoscope 200 by the endoscope reprocessor 1. The clogging detection operation may be executed a plurality of times during reprocessing. At a time point of start of the clogging detection operation, the fluid feeding pipeline 111, the detection pipeline 112 and the working fluid pipeline 113 of the endoscope connection tube 100 are respectively in states of being connected to the endoscope pipeline connection portion 16, the detection pipeline connection portion 62 and the working fluid pipeline connection portion 83, as illustrated in FIG. 2. At the time point of start of the clogging detection operation, the holding portion 102 of the endoscope connection tube 100 engages with the endoscope 200.

At the time point of start of the clogging detection operation, the fluid delivery pump 33 of the fluid supply source 60 and the air compressor 82 of the working fluid supply source 80 are in a stopping state. In other words, at the time point of start of the clogging detection operation, the seal portion 104 of the endoscope connection tube 100 is located in the second position where the seal portion 104 is separated from the pipe sleeve 202.

In the clogging detection operation, first in step S100, the control unit 5 starts supply of the working fluid by the working fluid supply source 80. More specifically, the control unit 5 brings the exhaust valve 84 into a closed state, and starts an operation of the air compressor 82. By execution of step S100, air that is a working fluid at a predetermined pressure is fed into the cylinder portion 103a of the switch portion 103 via the working fluid pipeline 113. Note that the control unit 5 may temporarily stop the operation of the air compressor 82 if the pressure in the space 103d of the cylinder portion 103a is kept at a predetermined value or more.

Accordingly, by execution of step S100, the switch portion 103 causes the seal portion 104 to move to the first position. In other words, after execution of step S100, the close contact surface 104a of the seal portion 104 is in a state of being in close contact with the pipe sleeve 202 as illustrated in FIG. 4.

Next, in step S110, the control unit 5 starts delivery of the fluid into the detection pipeline 112 by the fluid supply source 60. More specifically, the control unit 5 switches the three-way valve 63 to the state where the fluid delivery pump 33 and the detection pipeline connection portion 62 are connected to each other, and thereafter starts the operation of the fluid delivery pump 33. By execution of step S110, the fluid is fed into the detection pipeline 112 by the fluid supply source 60.

Next, in step S120, the control unit 5 determines whether or not the flow of the fluid in the detection pipeline 112 is detected by the detection portion 70. More specifically, in the present embodiment, the control unit 5 determines that the flow of the fluid in the detection pipeline 112 is not detected by the detection portion 70 when the flow rate of the fluid, which is detected by the flow rate measurement portion 71 is zero. The control unit 5 determines that the flow of the fluid in the detection pipeline 112 is detected by the detection portion 70 when the flow rate of the fluid detected by the flow rate measurement portion 71 is a value exceeding zero.

As described above, the first end portion 112a of the detection pipeline 112 opens in the close contact surfaces 104a of the seal portion 104. Accordingly, when the close contact surfaces 104a of the seal portion 104 are in close contact with the pipe sleeve 202 ideally at the time of execution of step S120, the detection pipeline 112 is closed by the pipe sleeve 202, so that the flow of the fluid in the detection pipeline 112 is not detected by the detection portion 70. When the flow of the fluid in the detection pipeline 112 is not detected by the detection portion 70, the control unit 5 shifts to step S150, determines that there is no failure in the close contact state of the seal portion 104 and the pipe sleeve 202, and shifts to step S160 that will be described later.

When the close contact surfaces 104a of the seal portion 104 are separated from the pipe sleeve 202 at the time of execution of step S120, the detection pipeline 112 is not closed by the pipe sleeve 202, so that the fluid fed into the detection pipeline 112 from the fluid supply source 60 flows out from the first end portion 112a. Accordingly, when the close contact surfaces 104a of the seal portion 104 are separated from the pipe sleeve 202 at the time of execution of step S120, the flow of the fluid in the detection pipeline 112 is detected by the detection portion 70.

When the flow of the fluid in the detection pipeline 112 is detected by the detection portion 70, the control unit 5 shifts to step S130, and determines that there is a failure in the close contact state of the seal portion 104 and the pipe sleeve 202. In step S140, the control unit 5 executes a display operation of warning that there is a failure in the close contact state of the seal portion 104 and the pipe sleeve 202 to the user. In step S210, the control unit 5 stops a supply operation of the working fluid by the working fluid supply source 80, and a supply operation of the fluid by the fluid supply source 60.

In this way, the endoscope connection tube 100 and the endoscope reprocessor 1 of the present embodiment can detect whether or not there is a failure in the close contact state of the seal portion 104 and the pipe sleeve 202.

As a cause of occurrence of a failure in the close contact state of the seal portion 104 and the pipe sleeve 202, a mechanical failure or trouble of the endoscope connection tube 100 is conceivable, such as a case where the seal portion 104 is broken, and a case where movement of the seal portion 104 by the switch portion 103 is not performed correctly is conceivable. As a cause of occurrence of a failure in the close contact state of the seal portion 104 and the pipe sleeve 202, an operation error is conceivable, such as a case where an operation of engaging the holding portion 102 and the endoscope 200 with each other by the user is not performed correctly, and a case where an operation of connecting the working fluid pipeline 113 to the working fluid pipeline connection portion 83.

When the control unit 5 determines that there is no failure in the close contact state of the seal portion 104 and the pipe sleeve 202 in step S120 and step S150, the control unit 5 starts delivery of the fluid into the fluid feeding pipeline 111 by the fluid supply source 60 in step S160. More specifically, the control unit 5 switches the three-way valve 63 to the state where the fluid delivery pump 33 and the endoscope pipeline connection portion 16 are connected to each other. Note that the control unit 5 may temporarily stop the operation of the fluid delivery pump 33 during a period of the switching operation of the three-way valve 63. By execution of step S160, the fluid is fed into the fluid feeding pipeline 111 by the fluid supply source 60.

In step S170, the control unit 5 determines whether or not the flow rate of the fluid that is delivered from the fluid supply source 60 is a predetermined threshold or more based on the measurement result by the flow rate measurement portion 71.

At the time of execution of step S170, the seal portion 104 and the pipe sleeve 202 are in a close contact state, so that all of the fluid which is delivered from the first end portion 111a of the fluid feeding pipeline 111 flows out into the treatment basin 2 after passing in the pipeline 201 of the endoscope 200. Accordingly, the flow rate of the fluid which is delivered from the fluid supply source 60 changes in response to a flow resistance of the fluid that occurs in the pipeline 201.

When the flow rate of the fluid that is delivered from the fluid supply source 60 is the threshold or more in step S170, the control unit 5 shifts to step S200, and determines that clogging such as a blockage or constriction does not occur to the pipeline 201 of the endoscope 200. The control unit 5 shifts to step S210, and the control unit 5 stops the supply operation of the working fluid by the working fluid supply source 80, and a supply operation of the fluid by the fluid supply source 60.

When the flow rate of the fluid that is fed from the fluid supply source 60 is less than the threshold in step S170, the control unit 5 shifts to step S180, and determines that clogging such as blockage and constriction occurs to the pipeline 201. Subsequently, the control unit 5 shifts to step S190, and the control unit 5 executes a display operation of warning that clogging occurs to the pipeline 201 of the endoscope 200 to the user by the display portion 8. The control unit 5 shifts to step S210, and stops the supply operation of the working fluid by the working fluid supply source 80, and the supply operation of the fluid by the fluid supply source 60. The control unit 5 brings the exhaust valve 84 into an open state, and releases pressure in the air delivery pipeline 81 and the working fluid pipeline 113. The clogging detection operation in the present embodiment ends here.

The flow feeding operation illustrated in FIG. 7 is executed when a fluid such as a medicinal solution such as a cleaning solution, an antiseptic solution or a sterilization solution, or rinse water is fed into the pipeline 201 during execution of reprocessing to the endoscope 200 by the endoscope reprocessor 1. Since it is necessary to bring the fluid into contact with not only the inside of the pipeline 201 but also the periphery of the pipe sleeve 202 at a time of execution of the fluid feeding operation, the seal portion 104 is required to be separated from the pipe sleeve 202.

At a time point of start of the fluid feeding operation, as illustrated in FIG. 2, the fluid feeding pipeline 111, the detection pipeline 112 and the working fluid pipeline 113 of the endoscope connection tube 100 are in states of being connected to the endoscope pipeline connection portion 16, the detection pipeline connection portion 62, and the working fluid pipeline connection portion 83 respectively. At the time point of start of the fluid feeding operation, the holding portion 102 of the endoscope connection tube 100 is engaged with the endoscope 200.

At the time point of start of the fluid feeding operation, the fluid delivery pump 33 of the fluid supply source 60 and the air compressor 82 of the working fluid supply source 80 are in a stopping state, and the exhaust valve 84 is in an opened state. Accordingly, at the time point of start of the fluid feeding operation, the seal portion 104 of the endoscope connection tube 100 is located in the second position where the seal portion 104 is separated from the pipe sleeve 202.

In the fluid feeding operation, at first in step S300, the control unit 5 starts delivery of the fluid into the detection pipeline 112 by the fluid supply source 60. More specifically, the control unit 5 switches the three-way valve 63 to the state where the fluid delivery pump 33 and the detection pipeline connection portion 62 are connected to each other, and thereafter starts an operation of the fluid delivery pump 33. By execution of step S300, the fluid is fed into the detection pipeline 112 by the fluid supply source 60.

Next, in step S310, the control unit 5 determines whether or not the flow of the fluid in the detection pipeline 112 is detected by the detection portion 70. More specifically, in the present embodiment, the control unit 5 determines that the flow of the fluid in the detection pipeline 112 is detected by the detection portion 70 when the flow rate of the fluid detected by the flow rate measurement portion 71 is a threshold or more.

As described above, the first end portion 112a of the detection pipeline 112 opens in the close contact surfaces 104a of the seal portion 104. Accordingly, when the close contact surface 104a of the seal portion 104 is separated from the pipe sleeve 202 at the time of execution of step S310, the detection pipeline 112 is not closed by the pipe sleeve 202. Accordingly, in this case, the fluid which is fed into the detection pipeline 112 from the fluid supply source 60 flows out from the first end portion 112a. Accordingly, when the close contact surfaces 104a of the seal portion 104 are separated from the pipe sleeve 202 at the time of execution of step S320, the flow of the fluid in the detection pipeline 112 is detected by the detection portion 70.

When the flow of the fluid in the detection pipeline 112 is detected by the detection portion 70 in step S310, the control unit 5 shifts to step S320 and determines that the seal portion 104 is separated from the pipe sleeve 202 normally. In other words, the case where the flow of the fluid in the detection pipeline 112 is detected by the detection portion 70 in step S320 occurs when movement of the seal portion 104 by the switch portion 103 is performed normally. The control unit 5 shifts to step S330, and executes step S360 that will be described later.

When the close contact surfaces 104a of the seal portion 104 are not separated from the pipe sleeve 202 at a time of execution of step S310, the detection pipeline 112 is closed by the pipe sleeve 202, and therefore the fluid in the detection pipeline 112 does not flow. Accordingly, when the close contact surfaces 104a of the seal portion 104 are not separated from the pipe sleeve 202 at the time of execution of step S310, the flow of the fluid in the detection pipeline 112 is not detected by the detection portion 70.

When the flow of the fluid in the detection pipeline 112 is not detected by the detection portion 70, the control unit 5 shifts to step S330 and determines that the seal portion 104 is not separated from the pipe sleeve 202. Subsequently, in step S340, the control unit 5 executes the display operation of warning that movement of the seal portion 104 by the switch portion 103 is not completed normally to the user by the display portion 8. In step S380, the control unit 5 stops the supply operation of the fluid by the fluid supply source 60.

After the control unit 5 determines that the seal portion 104 is separated from the pipe sleeve 202 normally in step S320, the control unit 5 shifts to step S360, and starts delivery of the fluid into the fluid feeding pipeline 111 by the fluid supply source 60. More specifically, the control unit 5 switches the three-way valve 63 to the state where the fluid delivery pump 33 and the endoscope pipeline connection portion 16 are connected to each other. Note that the control unit 5 may temporarily stop the operation of the fluid delivery pump 33 during the period of the switch operation of the three-way valve 63. By execution of step S360, a part of the fluid which is delivered from the first end portion 111a of the fluid feeding pipeline 111 leaks to the periphery of the pipe sleeve 202, and the remaining fluid is fed into the pipeline 201.

After the control unit 5 continues the delivery of the fluid into the fluid feeding pipeline 111 by the fluid supply source 60 for a predetermined time period in step S370, the control unit 5 shifts to step S380, and stops the supply operation of the fluid by the fluid supply source 60. The fluid feeding operation in the present embodiment ends here.

As described above, the endoscope connection tube 100 and the endoscope reprocessor 1 of the present embodiment are capable of automatically detecting whether or not the seal portion 104 is in the state of being separated from the pipe sleeve 202 based on the detection result of presence or absence of the flow of the fluid in the detection pipeline 112 by the detection portion 70. In other words, the endoscope connection tube 100 and the endoscope reprocessor 1 of the present embodiment are capable of automatically detecting whether or not the seal portion 104 is in the state of being in close contact with the pipe sleeve 202 based on the detection result of presence or absence of the flow of the fluid in the detection pipeline 112 by the detection portion 70.

As described above, when the seal portion 104 is in close contact with the pipe sleeve 202, the endoscope connection tube 100 is in a state of feeding the total amount of the fluid into the pipeline 201, whereas when the seal portion 104 is separated from the pipe sleeve 202, the endoscope connection tube 100 is in a state of leaking a part of the fluid to the periphery of the pipe sleeve 202. Accordingly, the endoscope connection tube 100 and the endoscope reprocessor 1 of the present embodiment are capable of detecting whether or not the endoscope connection tube 100 is in the state of feeding all of the fluid into the pipeline 201.

Note that the endoscope reprocessor 1 of the present embodiment described above has the configuration of detecting whether or not the endoscope connection tube 100 is in the state of feeding all of the fluid into the pipeline 201 at the time of the clogging detection operation, but a purpose and a timing of executing the operation of detecting whether or not the endoscope connection tube 100 is in the state of feeding all of the fluid into the pipeline 201 are not limited to the purpose and the timing of the present embodiment. For example, the endoscope reprocessor 1 may execute the operation of detecting whether or not the endoscope connection tube 100 is in the state of feeding all of the fluid into the pipeline 201 when executing the operation of feeding the fluid into only the pipeline 201. In this case, by executing the operation of feeding the fluid into only the pipeline 201, cleanability and disinfectability in the pipeline 201 by the endoscope reprocessor 1 can be improved.

In the endoscope connection tube 100 of the present embodiment, the close contact surface 104a of the seal portion 104 is in the annular shape that closely contacts the side surface 202c of the pipe sleeve 202 entirely in the circumferential direction, and the first end portion 112a of the detection pipeline 112 opens into the groove 104b that is provided to be engraved along the close contact surface 104a in the extending direction. Consequently, in the present embodiment, even when only a part in the circumferential direction of the close contact surface 104a is separated from the pipe sleeve 202, the detection pipeline 112 is not closed. Accordingly, the endoscope connection tube 100 and the endoscope reprocessor 1 of the present embodiment can reliably detect whether or not the seal portion 104 is in the state of being in close contact with the pipe sleeve 202 normally.

Figure 8:
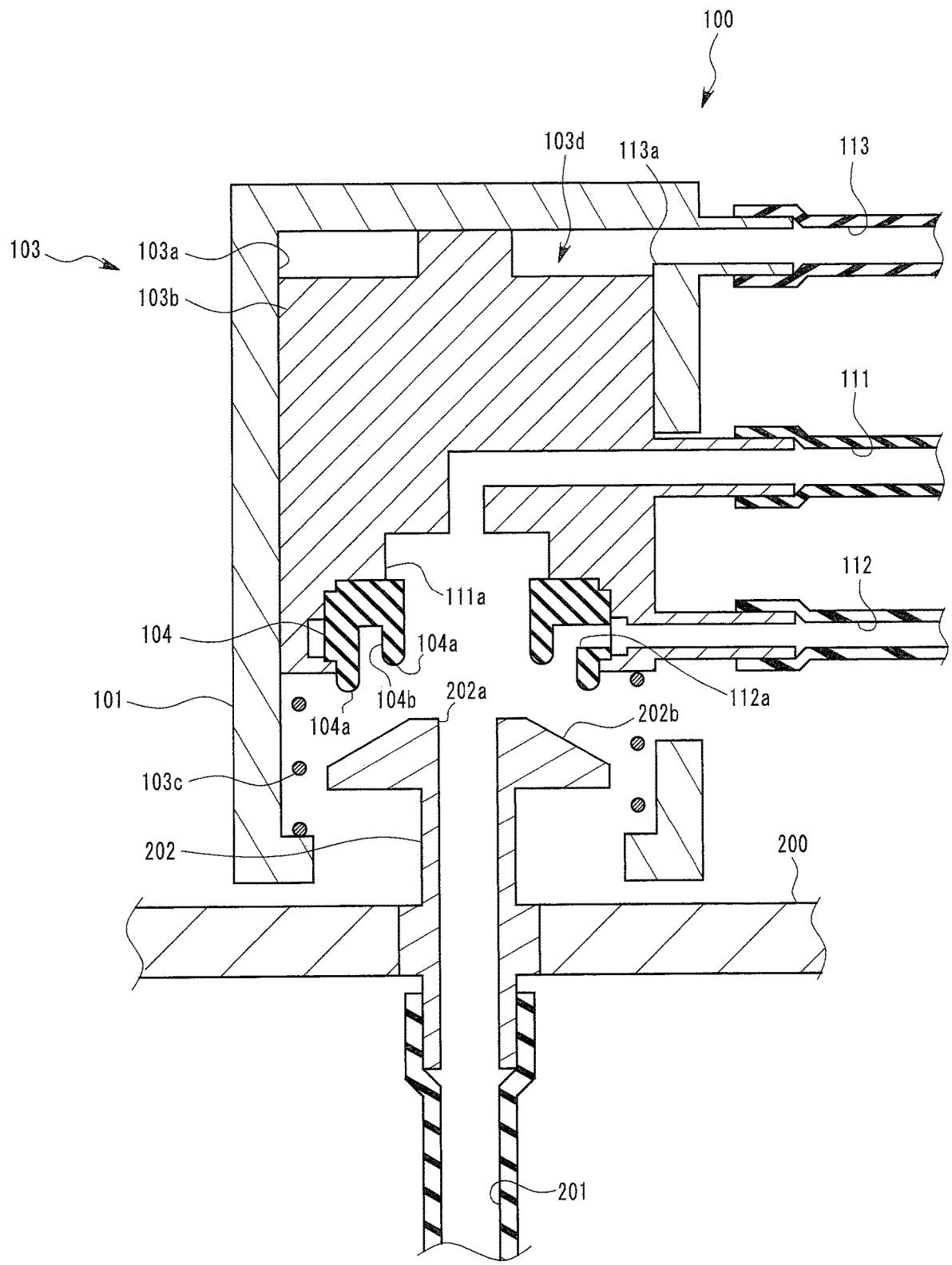
FIG. 8 is a sectional view illustrating a first modification of the endoscope connection tube of the first embodiment.
Figure 9:
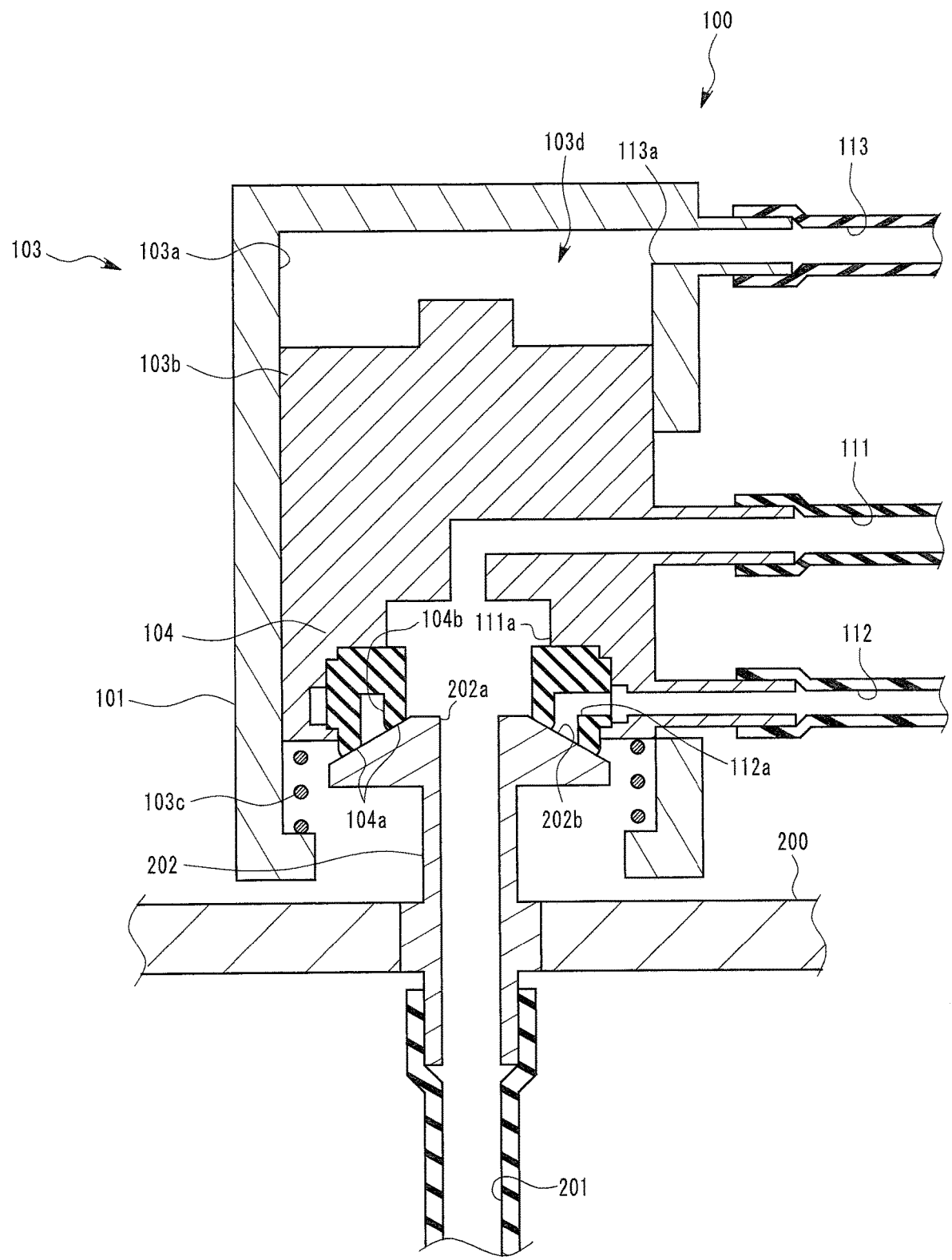
FIG. 9 is a sectional view illustrating the first modification of the endoscope connection tube of the first embodiment.

In the present embodiment described above, the seal portion 104 is in the annular shape in which the pipe sleeve 202 is inserted, and has the close contact surfaces 104a that closely contact the side surface 202c of the pipe sleeve 202, but the shape of the seal portion 104 is not limited to the shape of the seal portion 104 of the present embodiment. FIG. 8 and FIG. 9 illustrate a first modification of the seal portion 104. FIG. 8 illustrates a state where the seal portion 104 is located in the second position in the present modification, and FIG. 9 illustrates a state where the seal portion 104 is located in the first position in the present modification.

The seal portion 104 of the present modification has the close contact surfaces 104a that closely contact the end surface 202b of the pipe sleeve 202. The opening portion 202a is formed in a center portion of the end surface 202b, and the end surface 202b has an annular surface that surrounds the opening portion 202a. The close contact surfaces 104a of the seal portion 104 are annular surfaces that are placed to face the end surface 202b, and the seal portion 104 connects the first end portion 111a of the fluid feeding pipeline 111 and an inside of the opening portion 202a to each other by closely contacting the end surface 202b so as to surround the opening portion 202a of the pipe sleeve 202. The first end portion 112a of the detection pipeline 112 opens in the close contact surfaces 104a.

Even in a mode in which the pipe sleeve 202 is not inserted inside the seal portion 104 when the seal portion 104 is located in the first position, as in the present modification, the endoscope connection tube 100 is capable of switching the state of leaking a part of the fluid to the periphery of the pipe sleeve 202, and the state of feeding all of the fluid into the pipeline 201 by causing the seal portion 104 to move.

In the present modification, the detection pipeline 112 is closed by the pipe sleeve 202 when the seal portion 104 is in the state of being in close contact with the pipe sleeve 202. Accordingly, the endoscope connection tube 100 and the endoscope reprocessor 1 of the present modification are capable of automatically detecting whether or not the seal portion 104 is in the state of being separated from the pipe sleeve 202 based on the detection result of presence or absence of the flow of the fluid in the detection pipeline 112 by the detection portion 70.

Figure 10:
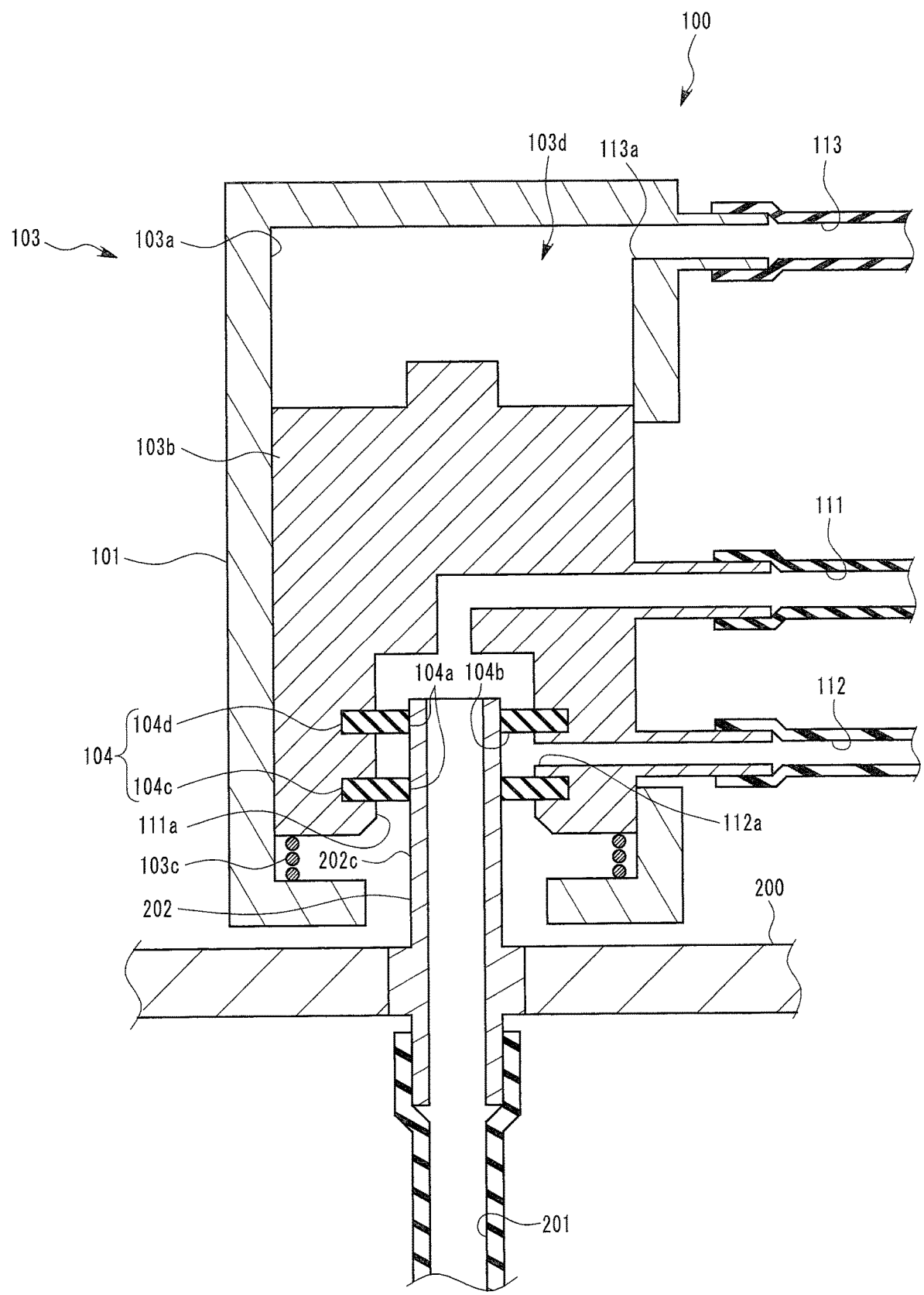
FIG. 10 is a sectional view illustrating a second modification of the endoscope connection tube of the first embodiment.

Next, FIG. 10 illustrates a second modification of the seal portion 104. The seal portion 104 of the present modification illustrated in FIG. 10 is divided into a plurality of members. More specifically, the seal portion 104 of the present modification is configured by a first seal member 104c and a second seal member 104d that are disposed to be separated along a depth direction of an opening of the first end portion 111a of the fluid feeding pipeline 111.

The second seal member 104d is disposed in a deeper position of the opening of the first end portion 111a of the fluid pipeline 111 than the first seal member 104c. The first seal member 104c and the second seal member 104d respectively include the annular close contact surfaces 104a that respectively closely contact the pipe sleeve 202. In the present modification, a gap between the first seal member 104c and the second seal member 104d is the groove 104b. In other words, in the present modification, the first end portion 112a of the detection pipeline 112 opens between the first seal member 104c and the second seal member 104d.

In the present modification like this, the first end portion 112a of the detection pipeline 112 is also in the state of having the periphery surrounded by the close contact surfaces 104a of the first seal member 104c and the second seal member 104d.

Accordingly, the endoscope connection tube 100 of the present modification is capable of switching the state of leaking a part of the fluid to the periphery of the pipe sleeve 202, and the state of feeding all of the fluid into the pipeline 201 by causing the seal portion 104 to move.

In the present modification, the detection pipeline 112 is also closed by the pipe sleeve 202 when the seal portion 104 is in the state of being in close contact with the pipe sleeve 202. Accordingly, the endoscope connection tube 100 and the endoscope reprocessor 1 of the present modification are capable of automatically detecting whether or not the seal portion 104 is in the state of being separated from the pipe sleeve 202 based on the detection result of presence or absence of the flow of the fluid in the detection pipeline 112 by the detection portion 70.

Second Embodiment

Hereinafter, a second embodiment of the present invention will be described. Hereinafter, only a difference from the first embodiment will be described, the same components as the components of the first embodiment will be assigned with the same reference signs, and explanation of the components will be properly omitted.

Figure 11:
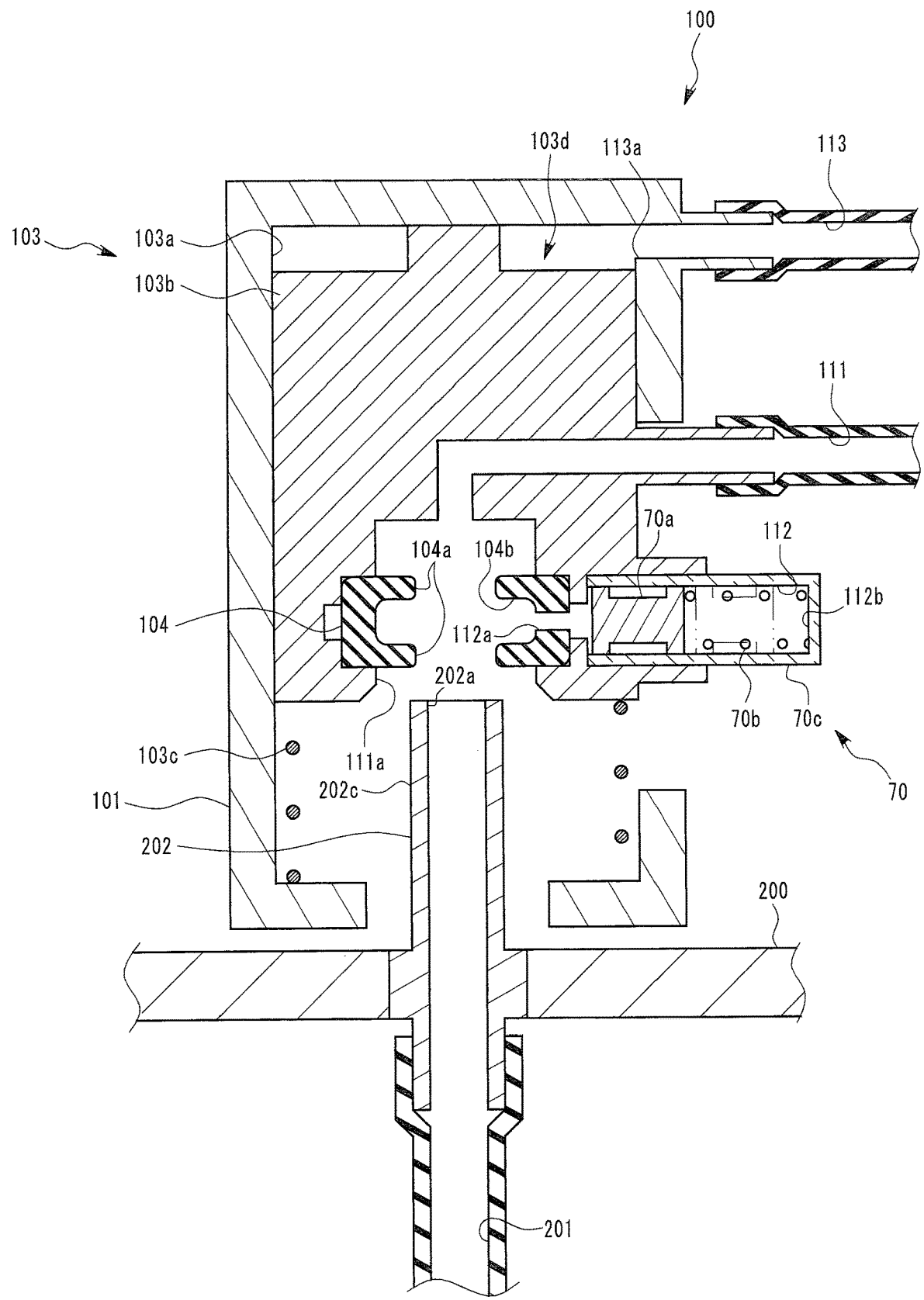
FIG. 11 is a sectional view illustrating a configuration of an endoscope connection tube of a second embodiment.
Figure 12:
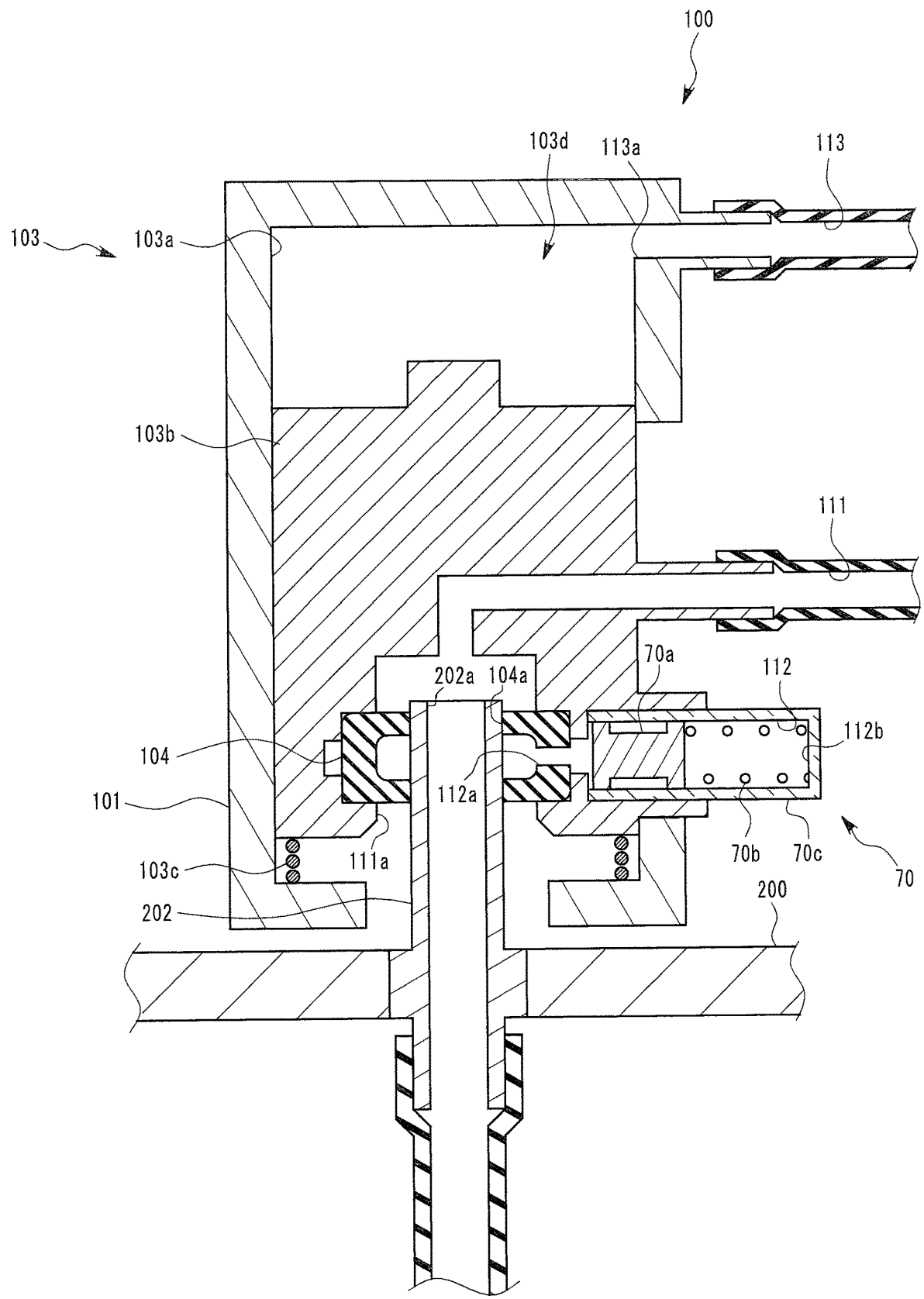
FIG. 12 is a sectional view illustrating the configuration of the endoscope connection tube of the second embodiment.
Figure 13:
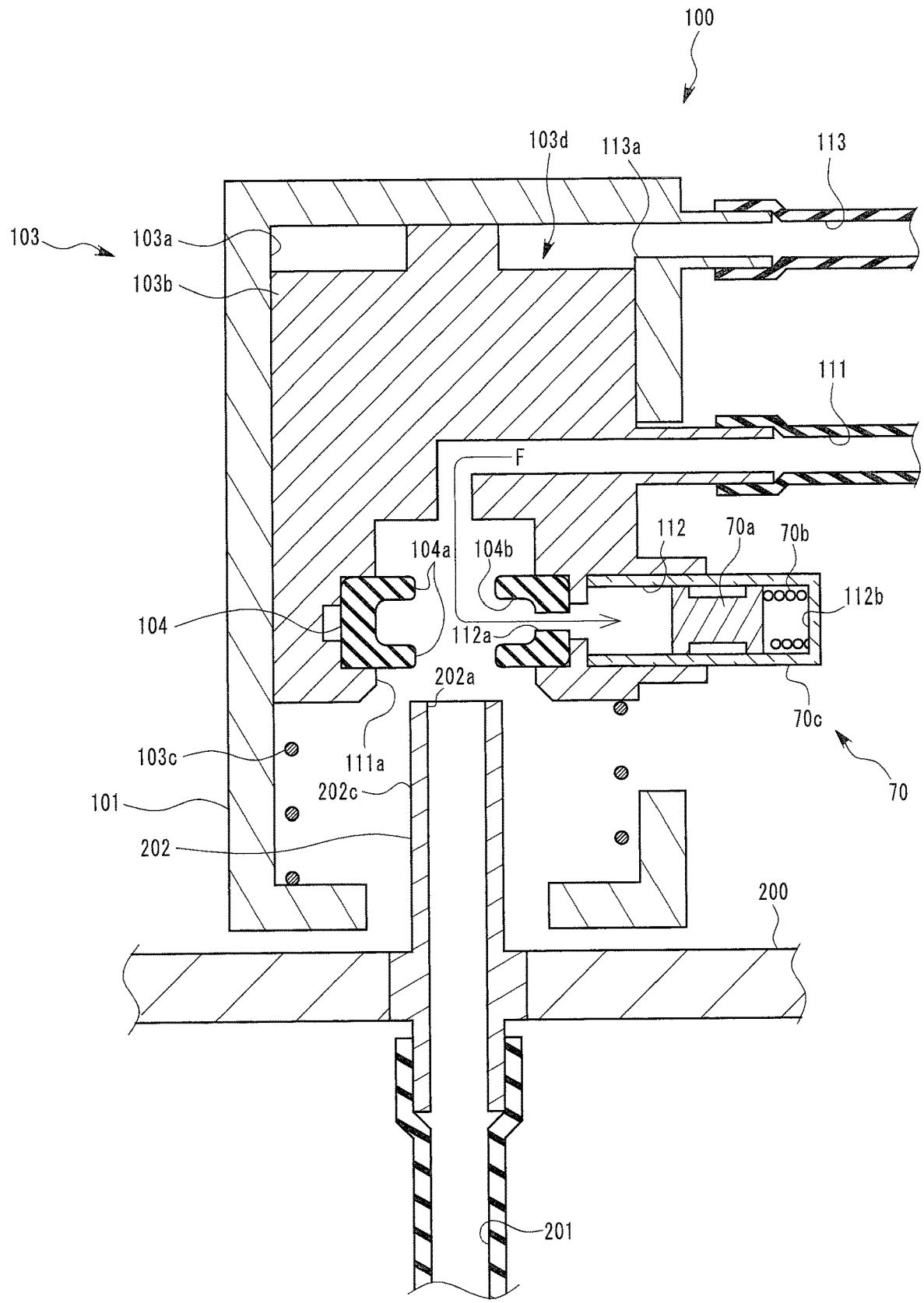
FIG. 13 is a sectional view explaining an operation of a detection portion of the second embodiment.

The present embodiment differs from the first embodiment in that the endoscope connection tube 100 includes the detection portion 70. FIG. 11, FIG. 12 and FIG. 13 are sectional views each illustrating a configuration of the endoscope connection tube 100 of the present embodiment.

The detection portion 70 of the present embodiment is disposed in the detection pipeline 112, and includes an advance and retreat portion 70a configured to move to advance and retreat in the detection pipeline 112, an urging portion 70b configured to urge the advance and retreat portion 70a to the first end portion 112a of the detection pipeline 112, and an observation window 70c that makes at least a part of a moving range of the advance and retreat portion 70a, of the inside of the detection pipeline 112, observable from outside of the detection pipeline 112.

The detection pipeline 112 of the present embodiment is in a cylindrical shape in which the second end portion 112b protrudes to outside from the connector portion 101, and is formed from a transparent material. The second end portion 112b of the detection pipeline 112 is closed. The advance and retreat portion 70a reaches a portion of the detection pipeline 112, which protrudes to outside from the connector portion 101, when the advance and retreat portion 70a moves to a side closest to the second end portion 112b, in the moving range. Accordingly, in the present embodiment, the portion of the detection pipeline 112, which is protruded from the connector portion 101, is the observation window 70c.

In the detection portion 70 of the present embodiment configured as above, the advance and retreat portion 70a moves in a direction of approaching the second end portion 112b when the fluid flows into the detection pipeline 112 from the first end portion 112a of the detection pipeline 112 as shown by an arrow F in FIG. 13. In this case, the advance and retreat portion 70a is located in a position visually recognizable from an outside through the observation window 70c.

In the detection portion 70 of the present embodiment, the advance and retreat portion 70a is held in a position close to the first end portion 112a of the detection pipeline 112 by an urging force of the urging portion 70b when there is no inflow of the fluid from the first end portion 112a of the detection pipeline 112. In this case, the advance and retreat portion 70a is located in a position that cannot be visually recognized from the outside through the observation window 70c.

Consequently, according to the present embodiment, the user confirms the position of the advance and retreat portion 70a through the observation window 70c, and thereby the user can know presence or absence of the inflow of the fluid from the first end portion 112a into the detection pipeline 112.

For example, when delivery of the fluid to the fluid feeding pipeline 111 from the fluid supply portion 60 is performed, if the advance and retreat portion 70a is in a state of being unable to be visually recognized through the observation window 70c, the user can determine that the seal portion 104 is in close contact with the pipe sleeve 202. When delivery of the fluid to the fluid feeding pipeline 111 from the fluid supply portion 60 is performed, if the advance and retreat portion 70a is in a state of being visually recognizable through the observation window 70c, the user can determine that the seal portion 104 is separated from the pipe sleeve 202.

Third Embodiment

Hereinafter, a third embodiment of the present invention will be described. Hereinafter, only a difference from the first embodiment will be described, the same components as the components of the first embodiment will be assigned with the same reference signs, and explanation of the components will be properly omitted.

Figure 14:
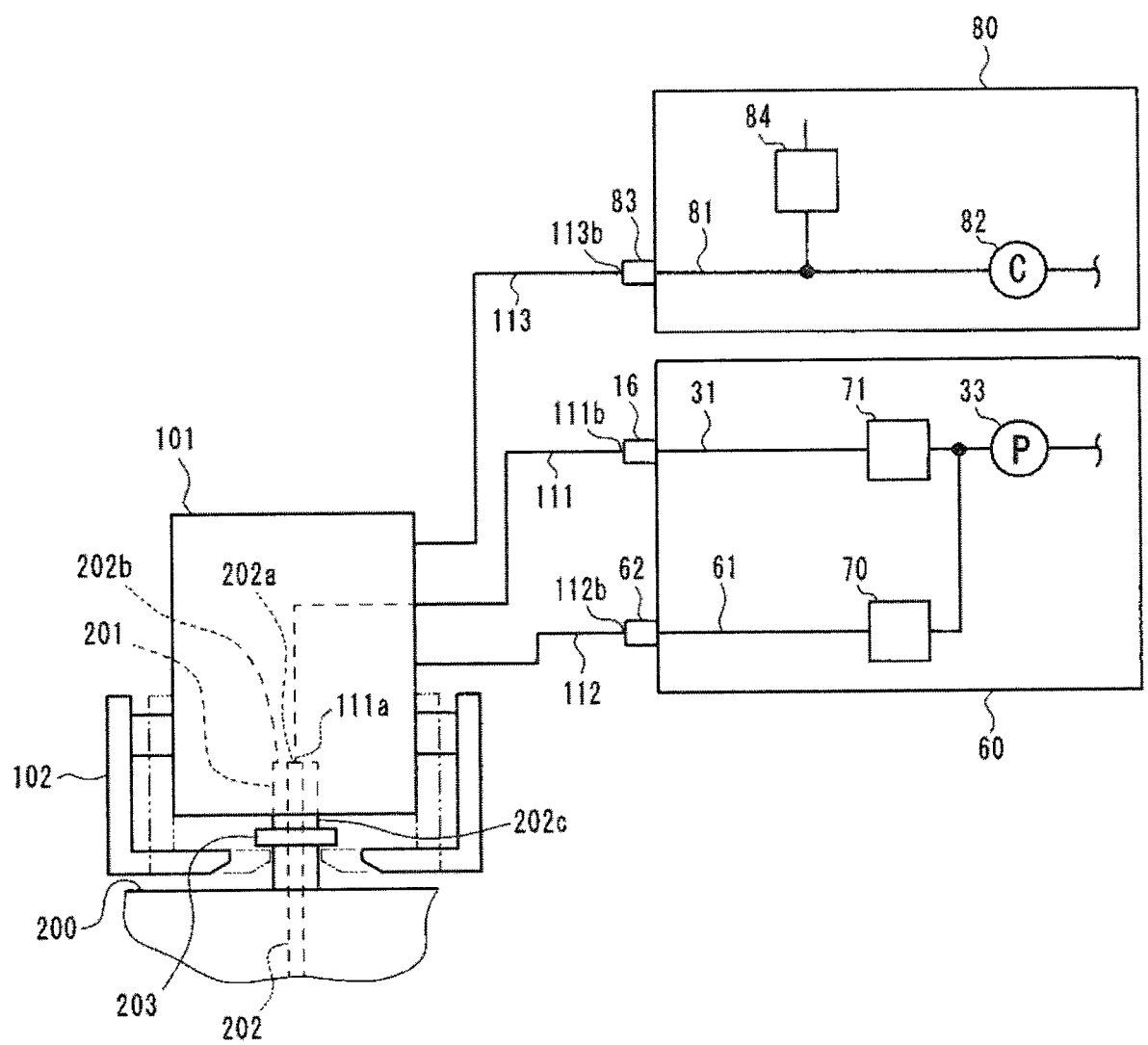
FIG. 14 is a diagram illustrating a configuration of a fluid supply portion of a third embodiment.

The present embodiment illustrated in FIG. 14 differs from the first embodiment in the configuration of the fluid supply portion 60. In the fluid supply portion 60 of the present embodiment, the detection portion 70 is placed as a separate component from the flow rate measurement portion 71.

As illustrated in FIG. 14, the detection fluid feed pipeline 61 of the present embodiment connects a section between the flow rate measurement portion 71 of the delivery pipeline 31 and the fluid delivery pump 33, and the detection pipeline connection portion 62. In a connection portion of the delivery pipeline 31 and the detection fluid feed pipeline 61, a valve mechanism such as a three-way valve is not provided. Accordingly, the fluid that is delivered from the fluid delivery pump 33 is fed into both of the fluid feeding pipeline 111 connected to the endoscope pipeline connection portion 16 and the detection pipeline 112 connected to the detection pipeline connection portion 62. The detection portion 70 of the present embodiment is a flow rate sensor that measures the flow rate of the fluid that flows in the detection pipeline connection portion 62.

The fluid supply portion 60 of the present embodiment delivers the fluid simultaneously to both the fluid feeding pipeline 111 and the detection pipeline 112 as described above. The fluid supply portion 60 of the present embodiment is capable of measuring flow rates in the respective fluid feeding pipeline 111 and detection pipeline 112.

Accordingly, in the endoscope connection tube 100 and the endoscope reprocessor 1 of the present embodiment, it is possible to simultaneously execute the operation of automatically detecting whether or not the seal portion 104 is in the state of being separated from the pipe sleeve 202, and the operation of delivering the fluid into the pipeline 201 via the fluid feeding pipeline 111, based on the detection result of presence or absence of the flow of the fluid in the detection pipeline 112 by the detection portion 70.

More specifically, in the clogging detection operation illustrated in FIG. 6, the operations of step S110 to step S150 and the operations of the step S160 to step S200 can be simultaneously executed. In the fluid feeding operation illustrated in FIG. 7, the operations of steps S300 to S320, and the operations of steps S360 to S370 can be simultaneously executed.

Accordingly, the endoscope connection tube 100 and the endoscope reprocessor 1 of the present embodiment can complete the clogging detection operation and the fluid feeding operation in a shorter time as compared with the endoscope connection tube 100 and the endoscope reprocessor 1 of the first embodiment.

Fourth Embodiment

Hereinafter, a fourth embodiment of the present invention will be described. Hereinafter, only a difference from the first embodiment will be described, the same components as the components of the first embodiment will be assigned with the same reference signs, and explanation of the components will be properly omitted.

Figure 15:
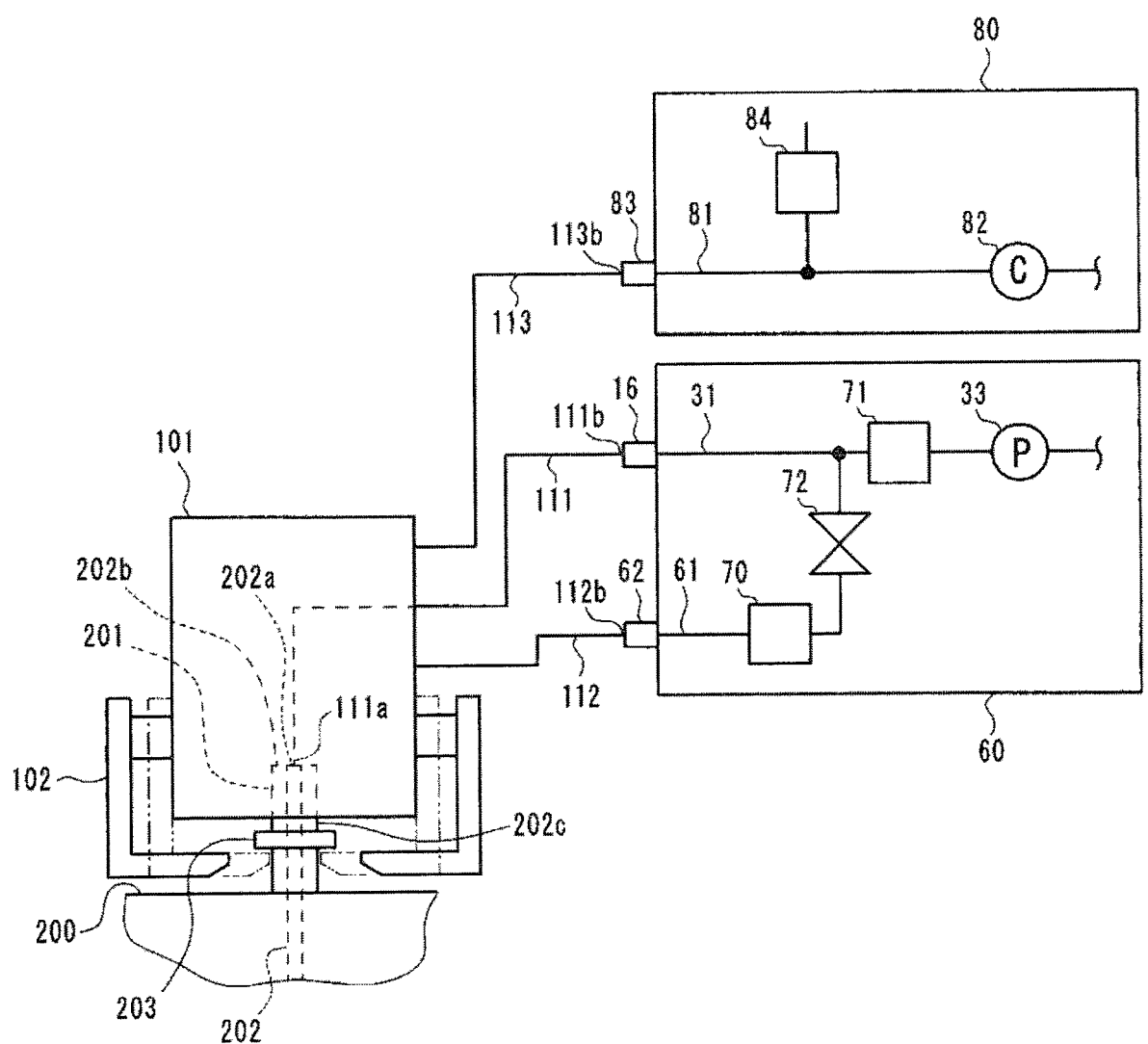
FIG. 15 is a diagram illustrating a configuration of a fluid supply portion of a fourth embodiment.

The present embodiment illustrated in FIG. 15 differs from the first embodiment in the configuration of the fluid supply portion 60. In the fluid supply portion 60 of the present embodiment, the detection portion 70 is placed as a separate component from the flow rate measurement portion 71.

As illustrated in FIG. 15, an on-off valve 72 is placed in the detection fluid feed pipeline 61 of the present embodiment. The detection portion 70 is a pressure sensor that is placed in a section between the on-off valve 72 of the detection fluid feed pipeline 61 and the detection pipeline connection portion 62. In the present embodiment, the three-way valve is not provided in the connection portion of the delivery pipeline 31 and the detection fluid feed pipeline 61.

The fluid supply portion 60 of the present embodiment simultaneously delivers the fluid to both of the fluid feeding pipeline 111 and the detection pipeline 112 as described above. In the present embodiment, the on-off valve 72 is brought into the closed state in the state where the fluid is fed at a predetermined pressure into the detection pipeline 112 by the fluid supply portion 60, and a subsequent change of the pressure of the fluid in the detection pipeline 112 (detection fluid feed pipeline 61) is measured by the detection portion 70, whereby presence or absence of the flow of the fluid in the detection pipeline 112 is detected.

For example, when the seal portion 104 is in close contact with the pipe sleeve 202, and the fluid in the detection pipeline 112 does not flow, a change does not occur to the pressure measured by the detection portion 70 after the on-off valve 72 is closed. When the seal portion 104 is separated from the pipe sleeve 202, and the fluid in the detection pipeline 112 flows out from the first end portion 112a, the pressure measured by the detection portion 70 decreases after the on-off valve 72 is closed.

In this way, the endoscope connection tube 100 and the endoscope reprocessor 1 of the present embodiment are also capable of automatically detecting whether or not the seal portion 104 is in the state of being separated from the pipe sleeve 202 based on the detection result of presence or absence of the flow of the fluid in the detection pipeline 112 by the detection portion 70.

Fifth Embodiment

Hereinafter, a fifth embodiment of the present invention will be described. Hereinafter, only a difference from the first embodiment will be described, the same components as the components of the first embodiment will be assigned with the same reference signs, and explanation of the components will be properly omitted.

The present embodiment differs from the first embodiment in the configuration of the endoscope connection tube 100. In the first embodiment, the seal portion 104 of the endoscope connection tube 100 has the contact surfaces 104a that closely contact or separate from the pipe sleeve 202. The seal portion 104 of the endoscope connection tube 100 of the present embodiment has the contact surfaces 104a that closely contact or separate from an outer surface 200a of the endoscope 200. The contact surface 104a of the present embodiment closely contact the outer surface 200a of the endoscope 200 so as to surround the opening portion 202a of the pipe sleeve 202.

Figure 16:
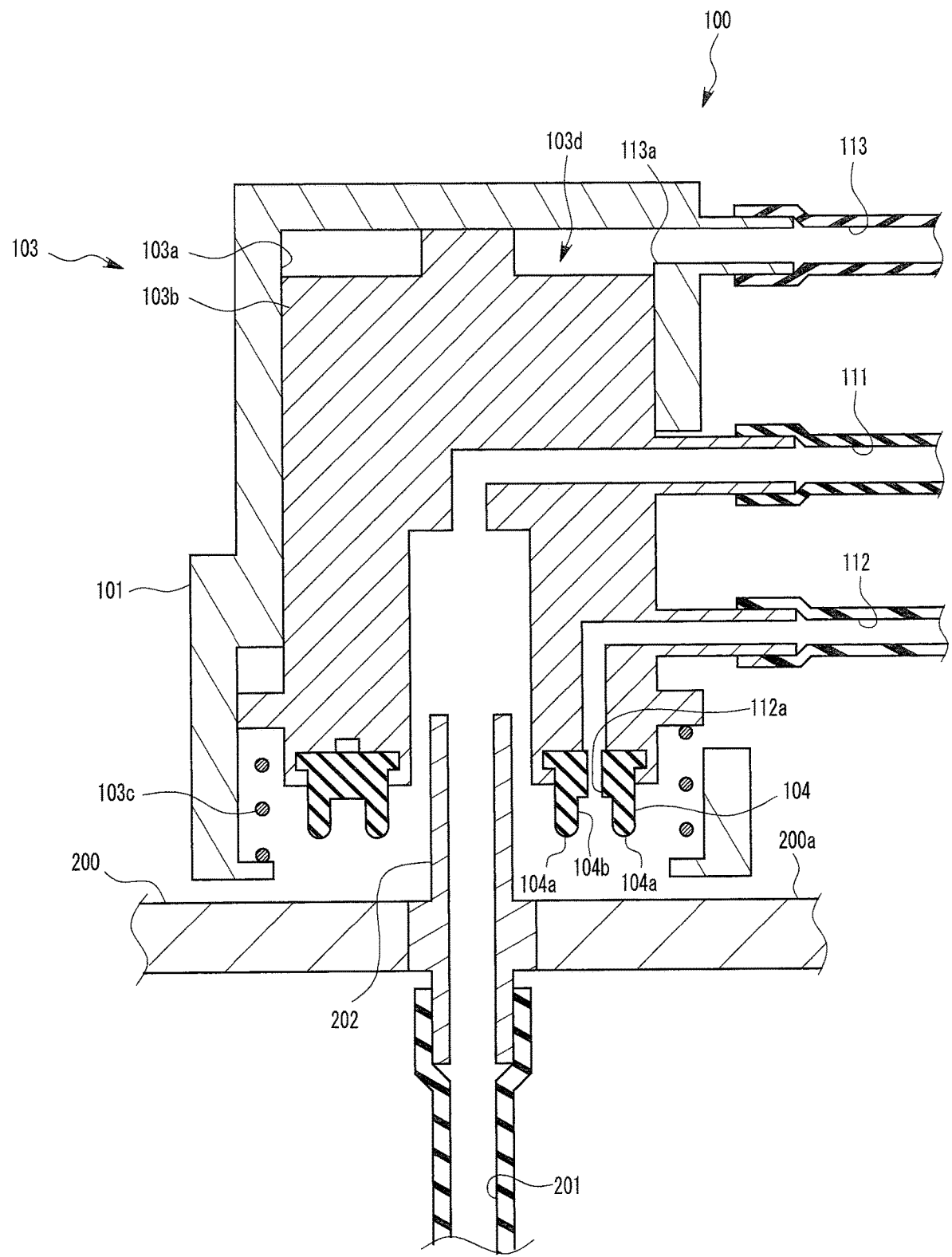
FIG. 16 is a sectional view illustrating a configuration of an endoscope connection tube of a fifth embodiment.
Figure 17:
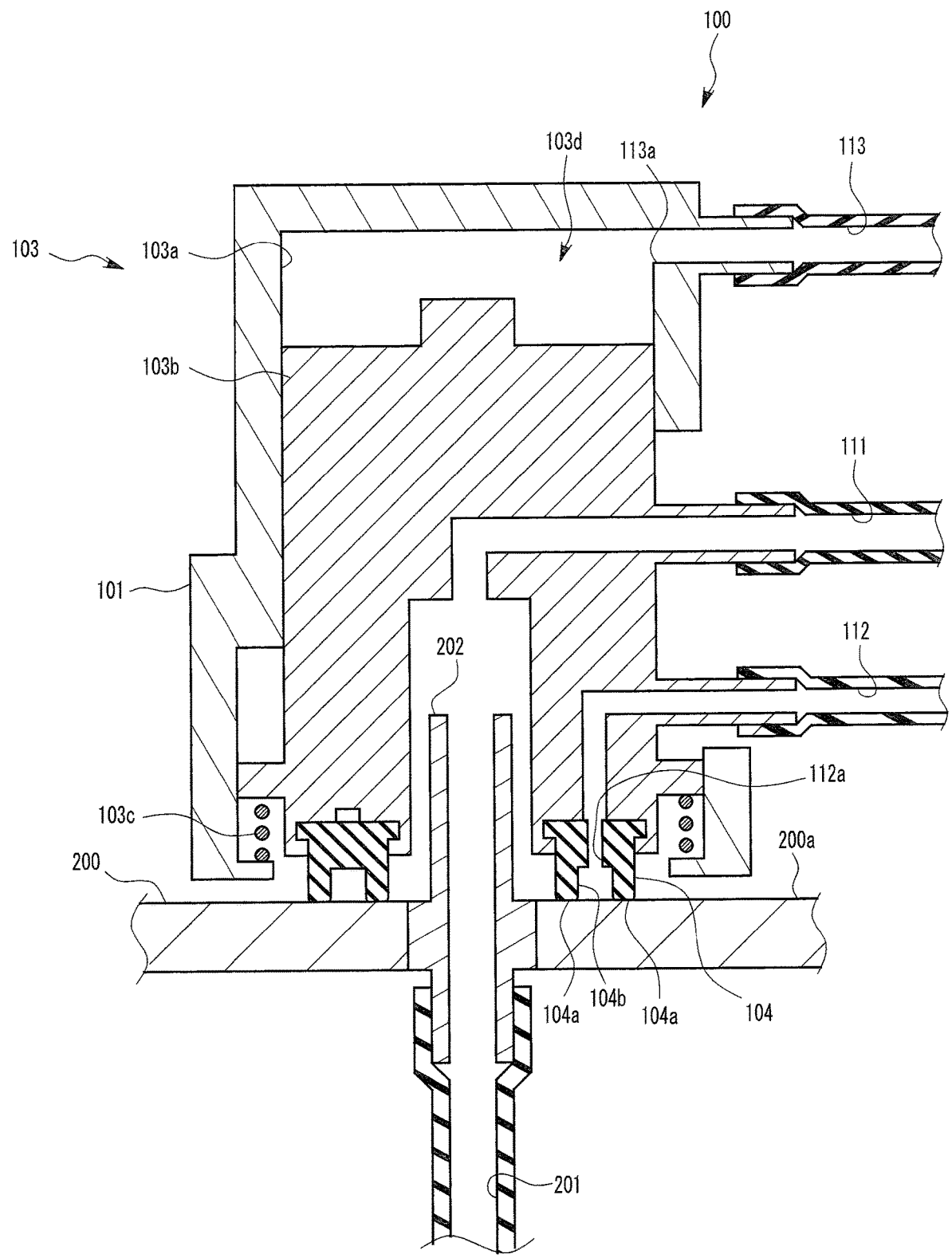
FIG. 17 is a sectional view illustrating the configuration of the endoscope connection tube of the fifth embodiment.

FIG. 16 and FIG. 17 each illustrate a sectional view of the endoscope connection tube 100 of the present embodiment. FIG. 16 illustrates a state where the close contact surface 104a is separated from the outer surface 200a of the endoscope 200, and FIG. 17 illustrates a state where the close contact surface 104a is in close contact with the outer surface 200a of the endoscope 200.

In the present embodiment, the opening of the first end portion 112a of the detection pipeline 112 provided in the close contact surfaces 104a is closed by the outer surface 200a of the endoscope 200 by the close contact surfaces 104a closely contacting the outer surface 200a of the endoscope 200. When the close contact surface 104a separates from the outer surface 200a of the endoscope 200, the first end portion 112a of the detection pipeline 112 is brought into an opened state.

According to the endoscope connection tube 100 and the endoscope reprocessor 1 of the present embodiment, it is also possible to detect whether or not the endoscope connection tube 100 is in the state of feeding all of the fluid into the pipeline 201, as in the first embodiment.

The present invention is not limited to the aforementioned embodiments but can be arbitrarily changed within the range without departing from the gist or the idea of the invention read from the claims and the entire description, and the endoscope connection tube and the endoscope reprocessor involving such changes are also included in the technical scope of the present invention.

What is claimed is:

1. An endoscope connection device comprising:
   a fluid feeding pipeline configured to feed fluid through an opening of the fluid feeding pipeline to an endoscope;
   a detection pipeline configured to feed fluid through an opening of the detection pipeline; and
   a seal configured to be brought into contact with a portion of the endoscope,
   wherein in a state where the seal is brought into contact with the portion of the endoscope, the seal and the portion of the endoscope reduce a flow of the fluid through the opening of the detection pipeline towards the endoscope.

2. The endoscope connection device according to claim 1, wherein the portion of the endoscope is a pipe sleeve of the endoscope.

3. The endoscope connection device according to claim 1, wherein the seal defines an annular groove provided along a surface of the seal configured to be brought into contact with the portion of the endoscope, and
   wherein the opening of the detection pipeline opens into the annular groove.

4. The endoscope connection device according to claim 1, wherein the portion of the endoscope is a pipe sleeve having a cylindrical shape,
   wherein the seal has an annular shape, and
   wherein an insider surface of the annular shape is configured to be brought into contact with the pipe sleeve to reduce the flow of the fluid through the opening of the detection pipeline towards the endoscope.

5. The endoscope connection device according to claim 1, further comprising:
   a switch configured to cause the seal to move between the state where the seal is brought into contact with the portion of the endoscope, and a state where the seal is separated from the portion of the endoscope.

6. The endoscope connection device according to claim 5, further comprising:
   a working fluid pipeline configured to feed a working fluid through an opening of the working fluid pipeline whereby the working fluid supplies a pressure to move the switch to cause the seal to move between the first state where the seal is brought into contact with the portion of the endoscope, and a second state where the seal is separated from the portion of the endoscope.

7. The endoscope connection device according to claim 1, comprising:
   a flow detector configured to detect the flow of the fluid fed through the detection pipeline.

8. An endoscope reprocessor comprising:
   the endoscope connection device according to claim 1;
   a flow detector configured to detect a flow of a fluid in the detection pipeline; and
   a fluid supply source comprising:
      a fluid delivery pump;
      a delivery pipeline configured to connect the fluid delivery pump and the fluid feeding pipeline to each other;
      a detection fluid delivery pipeline configured to connect the delivery pipeline and the detection pipeline; and
      a three-way valve placed in a connection portion of the delivery pipeline and the detection fluid delivery pipeline,
   wherein the flow detector is placed in a section between the fluid delivery pump and the three-way valve.

9. The endoscope reprocessor according to claim 8, wherein the flow detector is configured to detect a flow of the fluid in the fluid feeding pipeline.

10. The endoscope connection device according to claim 1, wherein the fluid feeding pipeline and the detection pipeline are different pipelines.

11. The endoscope connection device according to claim 1, wherein the endoscope is configured to separate the fluid feeding pipeline and the detection pipeline in the state where the seal is brought into contact with the portion of the endoscope.

12. The endoscope connection device according to claim 1, wherein the fluid flowing thorough the detection pipeline is configured to move from outward to inward of the seal.

13. The endoscope connection device according to claim 1, wherein the seal defines an opening on a circumference surface of the seal, and the opening of the seal connects to the opening of the detection pipeline.

14. The endoscope connection device according to claim 1, wherein the fluid feeding pipeline and the detection pipeline are not fluidly communicated with each other in the state where the seal is brought into contact with the portion of the endoscope.

15. The endoscope connection device according to claim 1, further comprising:
a controller configured to:
control a flow detector to detect the flow of the fluid fed through the detection pipeline;
determine the seal is brought into contact with the portion of the endoscope when the flow of the fluid fed though the detection pipeline is reduced; and
determine the seal is not brought into contact with the portion of the endoscope when the flow of the fluid fed though the detection pipeline is not reduced.

16. The endoscope cleaning device according to claim 15, wherein the controller configured to control a source to provide the fluid to be fed thorough the fluid feeding pipeline in response to determining that the seal is brought into contact with the portion of the endoscope.

17. The endoscope cleaning device according to claim 16, wherein the portion of the endoscope is a pipe sleeve of the endoscope, and
wherein in response to determining that the seal is brought into contact with the pipe sleeve of the endoscope, the controller configured to:
determine whether a flow rate of the fluid that is fed through the fluid feeding pipeline is equal to or above a threshold;
determine a clogging of an endoscope pipeline is present when the flow rate is under the threshold; and
determine a clogging of the endoscope pipeline is not present when the flow rate is equal to or above the threshold.

18. An endoscope connection device comprising:
a fluid feeding pipeline configured to feed fluid through an opening of the fluid feeding pipeline to an endoscope;
a detection pipeline configured to feed fluid through an opening at a first end portion of the detection pipeline, wherein a second end portion of the detection pipeline is closed;
a seal configured to be brought into contact with a portion of the endoscope, wherein in a state where the seal is brought into contact with the portion of the endoscope, the seal and the portion of the endoscope reduce a flow of the fluid through the opening of the detection pipeline; and
a flow detector comprises:
an advance and retreat portion disposed in the detection pipeline, and configured to move to advance and retreat in the detection pipeline;
an urging portion disposed in the detection pipeline, and configured to urge the advance and retreat portion towards the first end portion; and
an observation window configured to make at least a part of a moving range of the advance and retreat portion observable from outside of the detection pipeline.

19. The endoscope connection device according to claim 18, further comprising:
a switch configured to cause the seal to move between the state where the seal is brought into contact with the portion of the endoscope, and a state where the seal is separated from the portion of the endoscope; and
a working fluid pipeline configured to feed a working fluid through an opening of the working fluid pipeline whereby the working fluid supplies a pressure to move the switch to cause the seal to move to the first state where the seal is brought into contact with the portion of the endoscope, and a second state where the seal is separated from the portion of the endoscope.

20. An endoscope reprocessor comprising:
the endoscope connection device according to claim 8, wherein the portion of the endoscope comprises a pipe sleeve; and
a controller configured to, in a state where the seal is brought into contact with the pipe sleeve:
determine whether a flow rate of the fluid that is fed through the fluid feeding pipeline is equal to or above a threshold;
determine a clogging of an endoscope pipeline is present when the flow rate is under the threshold; and
determine a clogging of the endoscope pipeline is not present when the flow rate is equal to or above the threshold.

* * * * *